(12) United States Patent
Fuerst et al.

(10) Patent No.: US 9,910,007 B2
(45) Date of Patent: Mar. 6, 2018

(54) SENSOR DEVICE FOR DETECTING AN ANALYTE

(71) Applicant: Roche Diabetes Care, Inc., Indianapolis, IN (US)

(72) Inventors: Otto Fuerst, Viernheim (DE); Johannes Pill, Leimen (DE); Bernd Roesicke, Mannheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 640 days.

(21) Appl. No.: 14/087,347

(22) Filed: Nov. 22, 2013

(65) Prior Publication Data

US 2014/0083872 A1 Mar. 27, 2014

Related U.S. Application Data

(63) Continuation of application No. PCT/EP2012/059593, filed on May 23, 2012.

(30) Foreign Application Priority Data

May 23, 2011 (EP) .................................... 11167141

(51) Int. Cl.
*G01N 27/327* (2006.01)
*G01N 27/403* (2006.01)
(Continued)

(52) U.S. Cl.
CPC ..... *G01N 27/3271* (2013.01); *A61B 5/14532* (2013.01); *A61B 5/14546* (2013.01);
(Continued)

(58) Field of Classification Search
CPC ............. G01N 27/414; G01N 27/3275; G01N 27/3276; G01N 27/403; G01N 27/404
See application file for complete search history.

(56) References Cited

U.S. PATENT DOCUMENTS 4,324,256 A 4/1982 Vesterager
4,659,434 A 4/1987 Driscoll et al.
(Continued)

FOREIGN PATENT DOCUMENTS

EP 2228004 A1 9/2010
WO 9701091 A1 1/1997
(Continued)

OTHER PUBLICATIONS

Sensors 2008, 8, 1400-1458.*
(Continued)

*Primary Examiner* — Alexander S Noguerola
(74) *Attorney, Agent, or Firm* — Bose McKinney & Evans LLP

(57) ABSTRACT

A sensor device for detecting at least one analyte in a fluid, in particular in a body fluid, is disclosed. The sensor device includes at least one closed detector chamber and at least one electrical sensor having at least one sensor electrode. The detector chamber can be connected to the fluid in such a way that the analyte can penetrate into the detector chamber. The detector chamber includes at least one detector substance. The detector substance is designed to influence at least one electrical property of the electrical sensor, in particular at least one electrical property of the sensor electrode, depending on a concentration of the analyte in the detector chamber.

23 Claims, 6 Drawing Sheets

(51) Int. Cl.
*A61B 5/145* (2006.01)
*G01N 27/414* (2006.01)
*G01N 33/543* (2006.01)
*A61B 5/1473* (2006.01)
*G01N 27/404* (2006.01)

(52) U.S. Cl.
CPC ....... *A61B 5/14735* (2013.01); *G01N 27/403* (2013.01); *G01N 27/4145* (2013.01); *G01N 33/54366* (2013.01); *G01N 27/3276* (2013.01); *G01N 27/404* (2013.01)

(56) References Cited

U.S. PATENT DOCUMENTS

| | | | |
|---|---|---|---|
| 4,777,019 | A | 10/1988 | Dandekar |
| 4,846,937 | A | 7/1989 | Driscoll et al. |
| 4,916,075 | A | 4/1990 | Malmros et al. |
| 5,156,972 | A | 10/1992 | Issachar |
| 5,955,379 | A * | 9/1999 | Lennox ............... C12Q 1/003 422/82.02 |
| 6,210,326 | B1 | 4/2001 | Ehwald |
| 2003/0087296 | A1 | 5/2003 | Fujita et al. |
| 2006/0246478 | A1 * | 11/2006 | Yoo ............... G01N 33/54306 435/6.11 |
| 2007/0007148 | A1 | 1/2007 | Okada et al. |
| 2009/0242429 | A1 * | 10/2009 | Sitdikov ............... B82Y 5/00 205/792 |
| 2010/0155239 | A1 | 6/2010 | Sorensen et al. |
| 2010/0234237 | A1 * | 9/2010 | Yoo ............... B01L 3/50273 506/9 |
| 2011/0089957 | A1 * | 4/2011 | Sheppard, Jr. ..... G01N 27/3273 324/692 |
| 2011/0201099 | A1 * | 8/2011 | Anderson ............ G01N 21/05 435/287.2 |
| 2012/0043203 | A1 * | 2/2012 | Lin ......................... G01N 1/16 204/403.06 |
| 2012/0088990 | A1 * | 4/2012 | Bunge ............... A61B 5/14503 600/309 |

FOREIGN PATENT DOCUMENTS

| | | | |
|---|---|---|---|
| WO | 9719344 | A1 | 5/1997 |
| WO | 0004386 | A2 | 1/2000 |
| WO | 0237107 | A1 | 5/2002 |
| WO | 2006008505 | A1 | 1/2006 |
| WO | 2007130694 | A2 | 11/2007 |
| WO | WO2007130694 | * | 11/2007 |
| WO | 2009073625 | A1 | 6/2009 |
| WO | WO2010/123521 | * | 10/2010 |

OTHER PUBLICATIONS

Translation International Search Report downloaded Nov. 2, 2015 from WIPO website.*
Yasmin (Conducting Polymers, Jan. 2009, Master Thesis).*
Roberto Reverberi and Lorenzo Reverberi, "Factors affecting the antigen-antibody reaction," Blood Transfus 2007; 5: 227-240.*
Rahman, M, Kumar, P, Park, D, Shim, Y; "Electrochemical Sensors Based on Organic Conjugated Polymers", Sensors 2008, 8, 118-141.
Shinwari, M., Deen, M., Landheer, D., "Study of the electrolyte-insulator-semiconductor field-effect transistor (EISFET) with applications in biosensor design", Microelectronics Reliability 47 (2007) 2025-2057.
Beyer et al., "Recording of subcutaneous glucose dynamics by a viscometric affinity sensor", Diabetologia, Apr. 2001, vol. 44, Issue 4, 416-423.
Schuhmann, W., "Enzyme Biosensors Based on Conducting Polymers", Methods in Biotechnology, vol. 6, Techniques and Protocols, 143-156.
Schuhmann, W., "Conducting Polymers and Their Application in Amperometric Biosensors", ACS Symposium Series; Chapter 9, American Chemical Society, Washington, DC, 1994.

* cited by examiner

SENSOR DEVICE FOR DETECTING AN ANALYTE

CROSS REFERENCE TO RELATED APPLICATIONS

This is a continuation of application serial no. PCT/EP2012/059593filed May 23, 2012 and which claims priority from application serial no. EP 12 725 343.3 filed on May 23, 2011. Application serial no. EP 12 725 343.3 filed on May 23, 2012 is a related application.

FIELD OF THE INVENTION

The invention relates to a sensor device for detecting at least one analyte in a body fluid. Furthermore, the invention relates to a sensor system comprising at least one reader besides at least one sensor device according to the invention. Furthermore, the invention relates to a method for detecting at least one analyte in a fluid. Such sensor devices, sensor systems and methods are generally used in medical diagnostics, for example, in order to monitor body functions in vitro or in vivo. Examples include the continuous or discontinuous monitoring of analyte concentrations in at least one body fluid, such as, for example, interstitial fluid, urine, saliva or blood. Examples of appropriate analytes to be monitored include, individually or in any desired combination, glucose, cholesterol, lactate, at least one metabolite generally or other types of analytes and/or analyte combinations. In principle, however, the term analyte should be interpreted broadly and can comprise one or a plurality of chemical substances. In principle, however, the present invention is also applicable to other types of analytes and/or other types of fluid media, for example other types of gases and/or liquids, and/or to other fields of use, for example besides medical analysis environmental analysis, hazardous substance detection, workplace monitoring or other types of fields of use in chemistry, process engineering, combustion engineering, automotive engineering or other technical fields.

DESCRIPTION OF THE RELATED ART

The monitoring of specific body functions, in particular the monitoring of one or a plurality of concentrations of one or a plurality of analytes, is of major importance in the prevention and treatment of various diseases. Without restricting further possible applications, the invention is described hereinafter substantially with reference to blood glucose monitoring. In principle, however, the invention is also applicable to other types of analytes and/or the monitoring of other types of fluid media, such that, by way of example, as an alternative or in addition to a qualitative and/or quantitative detection of an analyte in a body fluid, at one or a plurality of analytes in other types of fluid media can be monitored.

Besides so-called point measurements, in which a sample of a body fluid such as, for example, urine, saliva, blood, interstitial fluid or other types of body fluid is deliberately taken from a user and examined with regard to the analyte concentration, continuous in vivo and/or vitro measurements are increasingly becoming established as well. In this regard, by way of example, a continuous glucose measurement in the interstitium (also designated as continuous monitoring, CM) has recently become established as an important method for management, for monitoring and for control of a diabetes status, for example.

In the meantime, in this case generally directly implanted electrochemical sensor elements are being used, which are often also designated as needle-type sensors (NTS). In this case, the active sensor region is brought directly to the measurement location, which is generally arranged in the interstitial tissue and using an enzyme (for example glucose oxidase, GOD, and/or glucose dehydrogenase), for example, converts glucose into an electrical charge which is related to the glucose concentration and can be used as a measurement variable. Examples of such transcutaneous measuring systems are described in U.S. Pat. No. 6,360,888 B1 or in US 2008/0242962 A1.

Present-day continuous monitoring systems are therefore generally transcutaneous systems. This means that the actual sensor is arranged below the user's skin. However, an evaluation and control part of the system (also designated hereinafter as a reader) is generally situated outside the user's body, i.e., outside the human or animal body. In this case, the sensor is generally applied by means of at least one insertion set, which is likewise described by way of example in U.S. Pat. No. 6,360,888 B1. Other types of insertion sets are also known. The bearing duration for a sensor is generally about one week. After that influences such as, for example, enzyme consumption and/or encapsulation in the body generally cause the sensitivity of the sensor to decrease, such that failure of the sensor is to be expected. Lengthening the bearing duration is therefore a current field of development.

Present-day sensors in human or veterinary diagnostics are therefore generally based on the principle of electrochemical and/or else photo-optical processes. In this case, the analyte to be detected is generally converted chemically via one or a plurality of intermediate steps by means of specific reagents. A primary signal can then be for example a color change and/or a charge equivalent. By way of example, as described above, glucose and oxygen from blood and/or interstitial fluid are converted to gluconolactone and $H_2O_2$ by the enzyme GOD in electrochemical sensors. The further conversion of the $H_2O_2$ then yields charge equivalents, for example two electrons. When there is an excess of the enzyme, a measurement signal is generally only dependent on the glucose concentration. However, generally sufficient oxygen has to be present, and the stability of the respective anode used during the electrochemical detection with respect to a redox reaction and a pH value is also required. Overall, this generally leads to ageing in the case of conventional sensor elements, such that continuous operation of such sensors is temporally limited.

Besides known sensor elements of this type for analyte detection, the prior art discloses numerous other sensor systems by means of which one or a plurality of analytes can be detected. Semiconductor sensors, for example so-called ISFETs, are known, for example, which can be used in chemical or medical diagnostics.

In this regard, DE 35 13 168 A1, for example, discloses a biosensor in which small basic building blocks of macromolecules are introduced into a layer near the surface facing a measurement medium via a gate region of a field effect transistor, for example. So-called biochips, for example, can be obtained in this way. DE 38 54 886 T2 discloses a sensor for carrying out immunoassays which comprises a film composed of semiconducting polymers having a front and a rear surface, and a plurality of electroconductive areas. Furthermore, an immunoassay sensor cell having an open upper and lower end with a double chamber insert is described.

Such known semiconductor structures or organic semiconductor structures are generally based on the fact that the semiconducting properties of a substrate material are influenced by chemical processes, for example by the binding or occupation of binding sites. In this case, a biological part, for example analyte-affinity structures such as proteins or nucleic acids, is linked to the semiconductor as intimately as possible. DE 35 13 168 A1 combats for example a problem of non-specific binding by means of a differential method on the basis of semiconducting polymers in the differential mode.

M. A. Rahman et al.: Electrochemical Sensors Based on Organic Conjugated Polymers, Sensors 2008, 8, 118-141, describe biosensors on the basis of semiconducting polymers in which, for example, a competitive immunological reaction or else a direct hybridization takes place. In this case, various concepts are described and compared with one another.

B.Em: ISFET, Theory and Practice, IEEE Sensor Conference Toronto, October 2003, discloses various embodiments of so-called ion-sensitive field effect transistors. Inter alia, an operational amplifier based on an ISFET is described here.

The prior art furthermore discloses a plurality of concepts for determining carbon dioxide. In this regard, U.S. Pat. No. 4,324,256, for example, describes a device for the transcutaneous measurement of a carbon dioxide partial pressure by means of a pH-sensitive measuring electrode behind a $CO_2$-permeable membrane. Since the pH value is a function of the $CO_2$ partial pressure, the carbon dioxide concentration can be determined by means of the pH electrode. Analogously, WO 2006/008505 A1 describes a physiological sensor device for measuring a $CO_2$ partial pressure. A membrane permeable to carbon dioxide is once again provided, said membrane closing off a chamber with two electrodes. WO 00/04386 A2 also describes a carbon dioxide sensor with a closed chamber, said sensor having a substantially water-tight wall and a membrane permeable to carbon dioxide. Two electrodes are provided in the chamber. U.S. Pat. No. 4,846,937 discloses a method for determining a carbon dioxide content in gaseous or liquid samples. A semipermeable sensor membrane is once again provided in order to close off a measurement space with a sensor electrode and an electrolyte. US 2010/0155239 A1 describes a planar $CO_2$ sensor device having an electrode with an ion-selective layer, an electrolyte layer and an outer layer.

EP 2 228 004 A1 describes an implantable, self-calibrating biosensor with a microfluidic circuit. In this case, two or more electrodes are arranged on an outer side of the microfluidic circuit. Furthermore, porous biochemical sensor materials are provided which are in contact with a body tissue after implantation.

DE 19 591 159 A1 describes a microsensor for determining the concentration of glucose and other analytes in liquid on the basis of affinity viscometry. In this case, use is made of a dialysis chamber containing a polymer system dispersed in water. Furthermore, a pressure-sensitive, volume-sensitive or flow-sensitive signal generator is provided, which supplies electrical signals according to the viscosity.

The known sensor concepts for diagnostic and non-diagnostic applications are confronted with a multiplicity of technical and medical challenges. Continuously measuring, diagnostic sensors, such as the CM sensors described above, for example, in contrast to the semiconductor structures mentioned above, are however usually used in the subcutaneous environment, that is to say in a moist milieu. One technical challenge in this case consists in particular in the fact that the analyte, for example glucose, from the interstitium or body fluid, has to pass into the sensor. In the case of customary sensor chemical systems generally set up as test chemical systems, for example, the analyte from the interstitium has to diffuse into a test chemical field through a specific sensor-side membrane and a suitable concentration gradient for the purpose of obtaining a diffusion-controlled reaction. In this case, the conversion becomes dependent on an enzyme quantity or enzyme activity. The membrane furthermore prevents parasitic effects from occurring, for example as a result of foreign molecules, in particular as a result of other redox-active substances, and being superimposed on the measurement signal. Furthermore, the membrane conversely is also intended to prevent substances from passing from the test chemical field and the sensor material into the body.

In customary electrochemical sensors, the measurement signals are generally conditioned by subsequent signal amplification, for example a charge current and/or an optical signal, analog/digital conversion and processing by means of a suitable microcontroller. The processing electronics generally consist of traditional silicon components. The signal processing unit downstream of the sensor is usually separated from the actual sensor by means of plug systems, for example owing to reasons relevant to production.

In most of the sensor systems mentioned above, ageing of the sensor generally limits the service life thereof. A mechanical loading of the relatively complicated sensor construction, whether in the case of conventional electrochemical analyte sensors for use in medical technology or in the case of the semiconductor sensors described, can also be limiting. In the case of subcutaneous applications, a relatively frequent change, that is to say a relatively frequent invasive intervention, is therefore necessary, for example a change with a weekly frequency.

In the case of semiconductor sensors and an influence of semiconductor properties, for example of silicon, specific binding sites with high activation energies are generally required for the docking of the analyte to be detected, which is generally possible with difficulty in direct contact with the moist milieu.

Furthermore, sensor production and production of a device for electronic post-processing generally take place in different production processes. In this regard, it generally has to be taken into consideration that different production processes, for example chemical production processes and traditional semiconductor processes, have to be combined for example in the case of the semiconductor sensors described above. Integration and reduction of structural size and reduction of production costs are therefore generally possible only to a limited extent.

A further technical challenge in the case of known sensor elements generally consists in the fact that traditional measured value acquisition usually takes place by means of a serial conversion from a detection step via a multi-stage chemical conversion and then via a signal amplification in a plurality of stages, followed or accompanied generally by at least one analog-to-digital conversion and/or an indication of the measured values. In this case, generally, owing to the multiple serial conversion of the measurement variable, noise in the respective predecessor stage is amplified in a downstream stage. In many known sensors, therefore, it is not possible adequately to comply with a basic principle of signal processing, namely amplifying the primary signal in the first stage to the highest possible extent.

A further technical challenge consists in the fact that electrochemical sensors for human diagnostics, in particular for subcutaneous use, generally have to be configured in a sterile fashion. Such sterilization generally takes place by means of a radiation sterilization method, since other methods, such as thermal and/or chemical sterilization methods, for example, would generally destroy the reaction chemical system relevant to the measured values. In many cases, however, the electronic components, for example based on silicon, integrated in the sensor, if appropriate, are damaged by the high radiation doses required, for example radiation doses of around 25 kgray or above 25 kgray, and would therefore have to be separated from the sensor during the sterilization process, which ultimately makes integration more difficult and/or impossible.

SUMMARY OF THE INVENTION

A problem addressed by the present invention is that of providing a sensor device for detecting at least one analyte which at least largely avoids the disadvantages described above. In particular, the sensor device is intended to enable a highly integrated design, optionally with already partly integrated electronics. Furthermore, the solution according to the invention is intended to enable in particular use in the context of subcutaneous analyte sensors.

This problem is solved by providing a sensor device, a sensor system and a method for detecting at least one analyte in a fluid comprising the features of the independent claims. Advantageous developments of the invention, which can be realized individually or in combination, are presented in the dependent claims.

A first aspect of the present invention proposes a sensor device for detecting at least one analyte in a fluid. As will be explained in even greater detail below, the sensor device can be designed in particular for complete or partial insertion into a body tissue of a user, for example into a subcutaneous interstitial tissue.

The analyte detection can take place qualitatively and/or quantitatively, wherein a quantitative detection, that is to say a detection of at least one analyte concentration, is preferred. The at least one analyte can be, in principle, one or a plurality of arbitrary analytes. It is particularly preferred if the at least one analyte to be detected is selected from the group consisting of: glucose; cholesterol; lactate or combinations of the substances mentioned and/or other primary substances and/or metabolites. The analyte detection can take place in a specific manner, in particular. The at least one fluid can be, in principle, an arbitrary gas and/or an arbitrary liquid. It is particularly preferred if the fluid is or comprises a liquid, in particular a body fluid, for example saliva, urine, blood, interstitial fluid or some other body fluid. The detection can take place in a body tissue, in particular.

The sensor device comprises at least one closed detector chamber and at least one electrical sensor having at least one sensor electrode. The electrical sensor can preferably be influenced electrically by the detector chamber, that is to say in particular by the content of the detector chamber. The detector chamber can be connected to the fluid, for example can be completely or partly inserted into a body tissue with the fluid, in such a way that the analyte can penetrate into the detector chamber, preferably reversibly. In this case, reversible penetration should be understood to a mean a process in which the analyte can penetrate into the detector chamber and can also leave the detector chamber again, for example on the basis of diffusion processes. The detector chamber comprises at least one detector substance, wherein the detector substance is designed to influence at least one electrical property of the electrical sensor, in particular at least one electrical property of the sensor electrode and/or of the detector chamber, depending on a concentration of the analyte in the detector chamber.

In this case, a detector chamber should be understood to mean, in principle, an arbitrary space which can be completely or partly filled with the detector substance and/or other substances, such that the latter can be prevented from leaving the detector chamber. In particular, as will be described in even greater detail below, the detector chamber can comprise a compartment in which a fluid, in particular liquid, medium is present. Said fluid medium can differ from the fluid in which the analyte is intended to be detected, but can also be configured completely or partly identically to this fluid or contain one or a plurality of identical constituents.

The detector chamber can have one or a plurality of chamber walls, in particular chamber walls which are completely or partly produced from plastic. In this case, in contrast to customary reaction vessels, a closed chamber should be understood to mean a chamber which prevents the detector substance from leaving the chamber. By way of example, the detector chamber can be configured in such a way that the detector substance cannot pass into a surrounding body tissue. In particular, the detector chamber can be enclosed on all sides, for example by at least one housing, in particular a housing with at least one membrane. However, other types of configurations of the detector chamber are also possible alternatively or additionally and have the effect that the detector substance cannot leave the detector chamber or can leave the latter only on an insignificant scale, for example in that in an implanted or inserted (both terms are used substantially synonymously) state over a period of at least one week not more than 1%, preferably not more than 0.1% and particularly preferably not more than 0.01% or even not more than 0.001% of the total quantity of the detector substance leaves the detector chamber. By way of example, the closed nature of the chamber can be realized in such a way that the latter comprises a medium into which the analyte can penetrate, but in which the detector substance is immobilized. By way of example, this can be a porous medium through which the fluid and/or the fluid medium and/or the analyte can penetrate, but in which the detector substance is enclosed and/or immobilized, such that the latter cannot leave the porous medium. By way of example, a porous plastic is involved. Furthermore, the closed nature of the chamber, in particular of the detector chamber, should be realized in particular in such a way that electrical components, for example electrodes, are electrically insulated in particular from one another, in particular in such a way that the fluid and/or the fluid medium cannot cause electrical short circuits.

The detector chamber can be configured in particular in an elongated fashion, for example by virtue of the chamber having a longitudinal extent with a dimension which exceeds an extent of the chamber transversely with respect to the longitudinal extent by at least a factor of 2, preferably by at least a factor of 5 and particularly preferably by at least a factor of 10. The detector chamber can have in particular an interior having a volume which is between 0.1 mm$^3$ and 10 mm$^3$, preferably between 0.5 mm$^3$ and 5 mm$^3$ and particularly preferably between 0.8 mm$^3$ and 2.2 mm$^3$. In particular, a chamber having a volume of 10 mm·10 mm·0.01 mm=1 mm$^3$ can be used.

An optional housing, which can close off the detector chamber on all sides or at least in sections relative to a surrounding medium, for example a body tissue, can be produced for example completely or partly from a plastic material. As will be described in even greater detail below, the at least one sensor electrode can also be at least partly a constituent of the housing of the detector chamber.

Furthermore, the detector chamber, alternatively or additionally, as will likewise be described in even greater detail below, can comprise at least one membrane, in particular at least one semipermeable membrane, wherein the membrane enables the analyte to penetrate reversibly into the interior of the detector chamber, in particular also encompassing emergence from the detector chamber, but the membrane prevents the at least one detector substance from escaping from the detector chamber.

The optional membrane can function in particular as a conduit for specific particles to pass into the detector chamber and/or out of the detector chamber. Alternatively or additionally, it can function as a barrier for the purpose of temporal control of the detection process. In particular, the membrane can be configured in a gastight fashion. The membrane can be configured in particular in such a way that it manifests its permeable or semipermeable properties only in a liquid, for example in aqueous solution.

In the context of the present invention, an electrode, in particular the sensor electrode, should be understood to mean a surface which can take up and/or transport electrical charges. By way of example, said electrode can be a surface of a dielectric designed for taking up electrical charges and/or a surface of an electrically conductive or electrically semiconducting element, which can be inorganic and/or organic in nature. Alternatively or additionally, the electrode can also have at least one conductive layer and/or the surface thereof, for example a metallic layer and/or an organic conductive layer. Said organic conductive layer can be applied in particular on a substrate, for example an insulator substrate, but the conductive layer is preferably applied on an electrically conductive element and/or electrically semiconducting element, for example an organic or inorganic semiconductor or conductor. Consequently, the electrode need not necessarily be a conductive layer or an electrically conductive element itself, but rather can in principle also be a surface of an electrically insulating or electrically conductive or semiconducting element. The sensor electrode can preferably be for example a gate electrode of a field effect transistor and/or can be an electrode and/or a plate of a capacitor.

As explained above, the electrical sensor is preferably intended to be able to electrically influenced by the detector chamber. This includes any electrical influencing, including polarization, application of charges, variation of a potential or variation of other electrical and/or dielectric properties. By way of example, the at least one sensor electrode of the electrical sensor may be able to be influenced by the detector chamber, for example by a potential of the sensor electrode being influenced by the detector chamber. Alternatively or additionally, charges can also be applied to the at least one sensor electrode directly or indirectly. Various types of influencing will be described in even greater detail below. Influencing by the detector chamber includes influencing by the content of the detector chamber, in particular influencing by the at least one detector substance and/or parts thereof and/or by the analyte or combinations of the possibilities mentioned. The sensor electrode can be part of the detector chamber or can be connected to the detector chamber in some other way, such that it can preferably be electrically influenced by the detector chamber. By way of example, the sensor electrode can be part of a housing of the detector chamber, for example of a chamber wall of the detector chamber. The sensor electrode can be exposed for example directly to the medium accommodated in the detector chamber, in particular to the detector substance. Alternatively or additionally, as will be described in even greater detail, at least one intermediate element, in particular at least one insulator layer and/or at least one protective layer, can be introduced between the sensor electrode and the interior of the detector chamber. It is particularly preferred, however, if the electrode is exposed directly to an interior of the detector chamber. From a physical standpoint, the interior of the detector chamber, for example a medium accommodated in the detector chamber, can itself be part of the sensor electrode.

Accordingly, a detector substance should be understood to mean a basically arbitrary substance which is designed to influence, preferably analyte-specifically, at least one electrical property of the electrical sensor, in particular at least one electrical property of the sensor electrode, depending on a concentration of the analyte in the detector chamber. By way of example, the detector substance can be designed and/or accommodated in the detector chamber in such a way that the analyte changes a charge distribution in the detector substance in the detector chamber and/or dielectric properties of the detector substance in the detector chamber. By way of example, the analyte can change, preferably reversibly, a permittivity and/or a relative permittivity, also called dielectric constant, detectable in each case for example as real or else as complex variables, of the detector substance, locally or else in a manner averaged over the detector chamber or a region thereof. The sensor device with the sensor electrode can be designed, on the basis of the sensor electrode by itself and/or in interaction with one or a plurality of further elements, such as, for example, at least one counterelectrode, to detect these analyte-governed changes in the charge distribution and/or these analyte-governed changes in the dielectric properties of the detector substance, for example by generation of at least one signal and/or by at least one signal change. The detection can take place statically and/or dynamically. By way of example, the detector substance can be designed in such a way that dielectric properties of the detector substance are influenced, in particular varied, by the presence of the analyte, wherein the sensor device can be designed for example to detect influences on an alternating electric field that are caused by this influencing of the dielectric properties. However, other measurement techniques can also be used alternatively or additionally.

As described above, the detector chamber can be connected to the fluid in such a way that the analyte can penetrate into the detector chamber. This penetration of the analyte can take place unidirectionally or, preferably, bidirectionally and/or reversibly. It is particularly preferred if the detector chamber is designed to enable a concentration equilibrium, in particular a diffusion-driven concentration equilibrium, of an analyte concentration within the detector chamber and outside the detector chamber. The diffusion of the analyte can take place selectively, in particular. By way of example, the detector chamber can be designed in such a way that the analyte can penetrate into the detector chamber, whereas emergence of other substances from the detector chamber into the environment, into the fluid and/or the body tissue for example, is preferably at least largely prevented. For this purpose, as will be described in even greater below, the detector chamber can comprise for example at least one membrane which enables the analyte to pass through, but which is preferably inpenetratable to other constituents of the fluid and/or the detector substance. In this case, a membrane should be understood to mean a single-layered or else multilayered element which enables passage of the at least one analyte, preferably a specific passage and/or selective passage, which is made possible only for the at least one analyte to be detected, but not for other substances, for example other constituents of the fluid, or only for a very limited number of further substances. The membrane can preferably be configured as at least partly porous material permeable to the analyte, for example a porous plastic material. The porous material can comprise for example pores which, in terms of their size, are adapted to passage of the analyte, but prevent molecules that are larger than the analyte from passing through.

By way of example, the membrane can comprise at least one membrane film. The membrane can be for example a semipermeable membrane which is impermeable to the at least one detector substance and/or constituents thereof. In particular, the membrane can be constructed in a film-like manner, for example with a thickness which falls below a lateral extent of the membrane by at least a factor of 10, preferably by at least a factor of 100 or more, in particular if no glucose saturation is present, for example if retarded transport is desired. By way of example, the membrane can have a thickness of less than 500 µm, in particular a thickness of less than 200 µm, particularly preferably a thickness of less than 100 µm, and in particular a thickness of at most 50 µm. Membranes, for example membrane layers applied to a carrier, can typically have masses per unit area of 5 to 20 mg/cm$^2$, for example. Given a density of approximately 1 g/cm$^3$, this implies membrane thicknesses of 50 µm to 100 µm, for example. Alternatively, the membrane can also have a thickness of 1 to 15 µm. The sensor device according to the present invention generally preferably consumes no glucose, for which reason essentially a fast setting of the equilibrium is desirable. Therefore, the membrane is preferably as thin as possible, for example a few micrometers thick, preferably 1 to 5 µm thick, wherein the membrane should preferably still be stable. Appropriate membrane materials include, in particular, plastic materials and/or polymers and/or materials on an organic basis, although arbitrary inorganic and/or organic materials can be used. In particular, one or a plurality of hydrophilic materials can be used as membrane material. The materials can be applied as a finished membrane or in situ, in particular as precursor material, for example dissolved in at least one solvent, and can then be shaped to form a membrane. The use of one or a plurality of the following materials as membrane materials is particularly preferable: a cellulose and/or a cellulose derivative, in particular a nitrocellulose and/or for example cellulose acetate and/or for example methyl cellulose; a polysulfone, for example polyethylene sulfone; a fluorinated polymer, for example polyvinylidene fluoride or FEP (fluorinated ethylene propylene); a polyether ether ketone (PEEK); a polyacrylotnitrile (PAN); a polycarbonate (PC); a, for example, hydrophilic, polyurethane (PU); a nylon; a regenerated cellulose. As an alternative or in addition to the materials mentioned and/or combinations thereof, other materials can also be used for the at least one membrane. If the membrane comprises a porous material, then the membrane preferably has a median pore size $d_{50}$ of between 1 µm and 10 µm, preferably between 2 µm and 5 µm. In principle, the membrane can also be without pores, in particular without pores which could be considered in a manner differentiated as such from the membrane material. By way of example, the analyte, in particular glucose, can penetrate in a diffusion-controlled manner through the thin membranes, which are preferably only a few µm thick and/or substantially pore-free, for example in such a way that preferably no glucose saturation can occur. In the case of the sensor device according to the invention, which preferably has no glucose consumption, for example a rapid equilibrium setting, for example by pores and/or by means of a rapid diffusion, for example through a pore-free membrane, is preferred. In particular, the membrane should have a high "effective diffusion coefficient" for the analyte, in particular glucose, and preferably prevent undesirable diffusion of other substances and preferably have mechanical stability. Therefore, the membrane should preferably have no pores or have selective pores and/or should have a high diffusion coefficient for the analyte, in particular for glucose.

As an alternative or in addition to the use of at least one membrane arranged between an interior of the detector chamber and an external space, for example the external fluid and/or the body tissue, the detector chamber can also comprise one or a plurality of further elements which enable the analyte to penetrate into the detector chamber, whereas emergence of detector substance from the detector chamber into the surrounding fluid is preferably prevented.

As described above, the detector substance is designed to influence at least one electrical property of the electrical sensor, in particular at least one electrical property of the sensor electrode. This can be for example a direct influencing of the sensor electrode, for example by a charge carrier density and/or a charge and/or a conductivity of the sensor electrode and/or a current through the sensor electrode being influenced directly or indirectly. Alternatively or additionally, however, this influencing can also be an influencing of an arrangement which comprises the sensor electrode and/or another constituent of the electrical sensor.

An influencing of the at least one electrical property of the electrical sensor depending on a concentration of the at least one analyte in the detector chamber, for example in a fluid accommodated in the detector chamber, in particular a liquid, should be understood to mean a property wherein the at least one property changes continuously or discontinuously at least without a certain concentration range with the concentration of the analyte. It is particularly preferred if this influencing takes place in such a way that there is an unambiguous, preferably linear, relationship, in particular a correlation, for example in the form of a function or mapping, between the at least one electrical property and the analyte concentration. By way of example, there can be a relationship by which a value of the electrical property is respectively assigned a value of the analyte concentration, in particular precisely a discrete value. The influencing can take place by the analyte itself and/or by the detector substance and/or by an interaction between the analyte and the detector substance, which can take place without or with complete or partial conversion of the analyte, as will be explained in even greater detail below.

The sensor device in accordance with the above description can be advantageously developed in various ways which can be combined with one another in any desired manner. As explained above, the detector chamber can be designed in particular to enable a reversible exchange of the analyte between an interior of the detector chamber and an environment of the detector chamber, in particular a surrounding body tissue. As explained above, this can take place in various ways.

The detector chamber, in particular at least a housing of the detector chamber which encloses an interior of the detector chamber, preferably completely, can have in particular at least one membrane, as explained above, in particular at least one analyte-specific membrane. This membrane can be designed in particular to enable the analyte to penetrate into the detector chamber reversibly, and preferably to retain the at least one detector substance in the detector chamber. The detected analyte can leave the detector chamber again in the case of reversible penetration for example independently, preferably by diffusion. The reversible penetration can comprise in particular an exchange of the analyte in the detector chamber. An exchange, in particular a complete exchange, of the analyte in the detector chamber within a specific time period is desirable, wherein the time period, for example a measurement time constant, should preferably be slightly shorter than a time period, for example a system time constant, in which for example the analyte concentration in the fluid changes. The system time constant can be determined in particular by an organism, in particular by the user's body, and for example not by the sensor device and/or a measuring arrangement. By way of example, if the measurement time constant is longer than the system time constant, in particular that of the organism, measurement errors can occur, for example. Preferably, the reversible penetration of the analyte into the detector chamber should enable the concentration of the analyte in the detector chamber to follow, in particular near-instantaneously, a change in the analyte concentration in the fluid, in particular with the shortest possible time delay. In particular, the membrane should be configured in such a way that the analyte concentration in the detector chamber correlates with the concentration of the analyte outside the detector chamber; preferably, these two concentrations should be at equilibrium or, in the case of an imbalance, equilibrium should be established in the shortest possible time, in particular within a time period in which for example the analyte concentration in the fluid changes, for example within a time period in which the concentration of glucose in a human body varies.

The detector chamber can be filled in particular at least partly with a liquid medium, in particular an aqueous medium. The at least one detector substance can be wholly or partly contained, for example dispersed and/or dissolved and/or emulsified, in the at least one liquid medium or can also itself be a constituent of the liquid medium, for example by said detector substance completely or partly itself constituting a liquid medium. Alternatively or additionally, however, as will be explained in even greater detail below, said at least one detector substance can also be present in a manner bound in the detector chamber, such that freedom of movement of the detector substance is restricted at least within certain limits. By way of example, the detector substance can be completely or partly and directly or indirectly bound to at least one wall of the detector chamber and/or to some other medium, for example a porous medium, in the interior of the detector chamber. By way of example, the detector substance can be directly or indirectly bound to a chamber wall itself or else an electrode of the electrical sensor, for example the at least one sensor electrode. This binding can take place directly or indirectly, for example directly or with interposition of at least one intermediate layer and/or at least one spacer.

In addition to the sensor electrode, the electrical sensor can furthermore comprise at least one counterelectrode, which can be configured for example as an auxiliary electrode. The counterelectrode can preferably be configured as an electrode, in particular as a conductive electrode, or as an electrode or a plate of a capacitor. The at least one counterelectrode can be wholly or partly a constituent of the housing of the detector chamber. The sensor device can be designed to particular to apply at least one electrical potential to the counterelectrode. The application of the at least one electrical potential can preferably be obtained by means of the positioning of electrical charge on and/or in the counterelectrode. By way of example, the at least one electrical potential can be applied to the counterelectrode via an electrical line. By way of example, the counterelectrode can have an electrically conducting or semiconducting region to which the at least one electrical potential can be applied by the application of an electrical voltage and/or of an electric current. The electrical voltage and/or the electric current can be, in principle, a DC voltage and/or a DC current. Preferably, the applied electrical voltage and/or the electric current can be a temporally variable, in particular regulable, signal, for example a voltage sequence and/or a current sequence. The voltage sequence and/or the current sequence can comprise for example at least one temporally periodic signal and/or a succession of signal pulses and/or a stepped signal profile. Preferably, the voltage sequence and/or the current sequence at the counterelectrode can be an alternating, in particular an alternating stepped, signal.

The detector chamber can be arranged at least partly between the sensor electrode and the counterelectrode. In principle, the detector chamber can also be arranged completely between the sensor electrode and the counterelectrode. Preferably, an arrangement can be chosen in such a way that the counterelectrode and the sensor electrode are not directly electrically conductively connected to one another, which can be realized for example by means of a suitable electrical insulation between the counterelectrode and the sensor electrode.

The sensor device can furthermore comprise at least one compensation sensor, which can be operated for example as part of a compensation circuit. In particular, the compensation sensor can comprise at least one reference sensor and/or can be configured wholly or partly as a reference sensor. The compensation sensor can preferably comprise at least one capacitor and/or at least one field effect transistor. A compensation sensor can be understood to mean a constituent of the sensor device which can supply by way of example a reference, for example a reference value. The sensor device can be configured in particular to combine the reference, for example the reference value, with at least one signal of the electrical sensor and to generate a common, compensated signal. In this regard, by way of example, an offset can be generated by means of the reference, which offset is subtracted from the signal of the electrical sensor. Other combinations of the reference with the signal are also conceivable alternatively or additionally. The compensation circuit can comprise the compensation sensor for example wholly or partly. The reference can preferably be an electrical property of the compensation sensor. The reference value can preferably be an electrical voltage and/or an electric current. The electrical property can be selected for example from the group consisting of: a charge carrier density; a charge; a conductivity; a current; a capacitance of the capacitor; a dielectric constant of a medium; an electrode spacing. Combinations of the properties mentioned and/or of other properties can also comprise the electrical properties. A compensation sensor can preferably be understood to mean a constituent of the sensor device which serves for example to compensate for at least one error variable. The compensation circuit and/or the compensation sensor can preferably serve to compensate for at least one error variable, for example at least one offset and/or a synchronism. The compensation sensor may preferably be able to be influenced electrically by the detector chamber, that is to say in particular by the content of the detector chamber. The compensation sensor, in particular the reference, can be used in particular for carrying out the detection of the at least one analyte independently of disturbing influences. The compensation sensor and/or the reference can furthermore be used for example in a method for calibrating and/or for gauging and/or for diagnosing at least one malfunction, in particular in the context of the detection of the analyte.

The compensation sensor can preferably be uninfluenced by the concentration of the analyte in the detector chamber. This situation of being uninfluenced by the concentration of the analyte in the detector chamber can be absolute, but can also encompass a suppression of an influence of the concentration of the analyte in the detector chamber. This situation of being uninfluenced can be realized, for example, by the compensation sensor comprising no receptor and/or no detector substance and/or by the compensation sensor comprising at least one detector substance and/or at least one receptor which the electrical sensor does not comprise.

The compensation sensor can preferably be embodied structurally identically to the electrical sensor, in particular with the proviso that the at least one electrical property of the compensation sensor is preferably as far as possible uninfluenced by the concentration of the analyte in the detector chamber. "Structurally identically" can be understood to mean, in particular, that the compensation sensor is constructed identically to the electrical sensor apart from components which make the electrical property of the compensation sensor dependent on the analyte, in particular on the concentration of the analyte, in the detector chamber, for example the detector substance and/or the receptor which can be comprised by the electrical sensor or at least one component of the detector substance which can be comprised by the electrical sensor.

The compensation sensor can comprise for example at least one compensation sensor electrode. The compensation sensor electrode can be configured in particular at least substantially structurally identically to the sensor electrode of the electrical sensor, with the proviso that the at least one electrical property of the compensation sensor electrode is preferably uninfluenced by the concentration of the analyte, at least down to a factor of $\frac{1}{10}$ in comparison with the influencing of the sensor electrode at the same analyte concentration. The detector substance can be connected to the sensor electrode, in particular to the sensor electrode of the electrical sensor. The compensation sensor electrode can be preferably, in particularly partly, free of the detector substance and/or the receptor, in particular the detector substance and/or the receptor which can be comprised in particular by the electrical sensor.

The electrical sensor and/or the compensation sensor can be incorporated in particular into an electrical bridge circuit and/or the compensation circuit. The bridge circuit can comprise for example at least one electrical resistance, in particular an electrical component which has an electrical resistance. The electrical resistance can be a real electrical resistance and/or a capacitive electrical reactance and/or an inductive electrical reactance. The electrical component can be in particular at least one capacitor and/or at least one ohmic resistor.

The detector substance can comprise in particular electrically charged particles of at least one type. These particles can preferably have a particle size $d_{50}$ which is less than 0.5 mm, particularly preferably less than 0.1 mm and particularly preferably less than 1 μm or even less than 100 nm, and/or that the particle size $d_{50}$ is preferably less than one tenth of a chamber dimension, in particular a dimension of the detector chamber and/or the volume of the detection chamber. In particular, microscopic and/or nanoscopic particles can therefore be involved in this case. Furthermore, alternatively or additionally, the electrically charged particles can also comprise electrically charged particles and/or electrically charged molecules. In the context of the present invention, electrically charged particles should generally be understood to mean particles which have a net charge and/or particles which have opposite electrical charges at different locations on one and the same particle, that is to say for example dipoles and/or multipoles. It is particularly preferred, however, if the electrically charged particles have a net charge of at least one elementary charge, preferably of at least two elementary charges or more.

The electrically charged particles can be accommodated as freely mobile particles in the detector chamber, for example in a liquid medium within the detector chamber, or, as will be explained in even greater detail below, can also be present in a bound manner, for example by means of one or a plurality of spacers. At any rate, however, the electrically charged particles should be able to carry out a movement within the detector chamber, in particular a movement perpendicularly to the at least one sensor electrode, for example a relative movement relative to the at least one electrical sensor. A charge redistribution of the electrically charged particles within the detector chamber is preferably possible, for example by virtue of said electrically charged particles being freely mobile or being connected via a moveable link to other elements, for example an inner wall of the detector chamber.

Preferably, the detector chamber and the detector substance are configured in such a way that an average distance between the electrically charged particles and the sensor electrode and/or a charge distribution within the detector chamber are dependent on the concentration of the analyte in the detector chamber. This can take place in various ways, which will be explained in even greater detail below by way of example. This can take place, for example, by the at least one analyte forcing the electrically charged particles closer to the at least one sensor electrode and/or closer to a chamber wall of the detector chamber. Alternatively, the at least one analyte can also displace the electrically charged particles from the at least one sensor electrode, such that the average distance between the electrically charged particles and the at least one sensor electrode rises. In turn alternatively or additionally, the charge distribution, in particular the distribution of the electrically charged particles, within the detector chamber can also be influenced in some other way, for example by an average distance between the electrically charged particles being varied, that is to say increased or decreased, by the analyte or by an interaction of the analyte with the at least one detector substance. In turn alternatively or additionally, specific inhomogenieties of the distribution of the electrically charged particles within the detector chamber can also be brought about by the analyte or by an interaction of the analyte with the detector substance, which, like the other effects as well, can influence the at least one electrical property of the electrical sensor.

The concentration of the analyte and/or a change thereof in the detector chamber can therefore preferably vary or influence a charge distribution and/or an average distance of the electrically charged particles in the detector chamber. As explained above and as will be explained in even greater detail below, the electrically charged particles can be freely mobile particles and/or else bound particles. The detector chamber and the detector substance can be configured in particular in such a way that the average distance between the electrically charged particles and the sensor electrode and/or the charge distribution within the detector chamber change(s) reversibly in the event of a change in the concentration of the analyte in the detector chamber.

The charge distribution within the detector chamber can be a continuous charge distribution and/or can also comprise a charge distribution in the form of differently charged layers within the detector chamber. Accordingly, for example at least two differently charged layers can be provided within the detector chamber, wherein the position and/or arrangement of said layers and/or a distance between the layers and the sensor electrode may be able to be influenced by the concentration of the analyte in the detector chamber. In this way, for example the position and/or the arrangement of said layers and/or the distance between the layers and the sensor electrode may be able to be influenced, preferably reversibly, by a change in the concentration of the analyte in the detector chamber. The variation or influencing of the average distance between the electrically charged particles in the detector chamber and/or the variation of the charge distribution within the detector chamber by the concentration of the analyte or a change thereof can therefore take place for example in such a way that the detector chamber and the detector substance are configured in such a way that layer formation of at least two layers having different electrical charges takes place within the detector chamber, wherein the distribution of the layers and/or the distance between the latter and the sensor electrode are/is dependent on the concentration of the analyte in the detector chamber, that is to say for example can be influenced by the concentration of the analyte and/or can be changed by a change in the concentration of the analyte, in particular reversibly.

Overall, therefore, the detector chamber and/or the detector substance can be configured in such a way that layer formation within the detector chamber and the geometry and/or the distances of said layer formation are dependent on the concentration of the analyte in the detector chamber and can be influenced by said concentration and/or can be varied by a change in said concentration, preferably reversibly. In this way, by way of example, the analyte concentration within the detector chamber can have an influence on an electrical signal of the sensor device. By way of example, as will be explained in even greater detail below, electric field strengths within a field effect transistor and/or a capacitance of a capacitor and/or dielectric properties of the detector chamber or of a part thereof may be able to influenced by the analyte concentration in the detector chamber. This influencing can be configured reversibly, in particular, for example in the form of a balancing process.

The electrically charged particles can have buffer properties in particular. Buffer properties should be understood to mean properties of a substance wherein the substance influences its environment to the effect that the pH value of the environment upon addition of an acid or a base changes to a significantly lesser extent than would be the case with an unbuffered system, that is to say in the absence of the substance. Preferably, the buffer properties include the fact that the substance has both acid properties and base properties.

Alternatively or additionally, the charged particles can form for example specific extended and/or ordered structures, for example by—provided that they are negatively charged—undergoing complexing with oppositely charged particles, for example with inorganic or organic cations. Since the negatively charged particles mentioned below are the corresponding bases of the acids mentioned, in particular mutual complexing of polycarboxylic acids, in particular mutual complexing of acid anions with metal cations and/or with protonated, in particular, organic, bases, for example with amines such as terminal alkyl diamines or heterocyclic compounds having, in particular a plurality of, basic nitrogen atoms, for example imidazole or bipyridines, can occur. Extended, but in particular well-defined, aggregates having residual net charge which can arise in this case, for example, could constitute for example more suitable detection substances than the original charged particles, for example since, in particular if present, an analyte- and charge-dependent orientation in the desired sense could be prevented. By way of example, more complex aggregates having a residual net charge could be formed, wherein a superordinate structure, for example linear structures, if appropriate also framework structures, would be predefined by a composition comprising the individual components.

The electrically charged particles can comprise in particular polyionic molecules, that is to say molecules which comprise at least one ionic group, in particular polyanionic molecules.

The electrically charged particles can comprise in particular at least one polycarboxylic acid. In particular, said at least one polycarboxylic acid can be a polycarboxylic acid of benzene, preferably a polycarboxylic acid selected from the group consisting of benzenedicarboxylic acid (H2), for example meta- or para-phthalic acid, preferably, since here the two negatively charged carboxyl groups are adjacent, ortho-phthalic acid, benzenetricarboxylic acid (H3), for example trimesic acid or trimellitic acid, benzenetetracarboxylic acid (H4), for example pyromellitic acid, benzenepentacarboxylic acid (H5) and benzenehexacarboxylic acid (H6) (mellitic acid); wherein in the mellitic acid a link to the spacer would generally be possible only via one of the six carboxyl groups, or dimers, trimers or oligomers or derivatives thereof.

As explained above, the detector substance can comprise in particular at least one spacer. Said spacer can be designed, in particular, to bind the electrically charged particles to the sensor electrode and/or a surface of the detector chamber at the sensor electrode. By way of example, this binding can take place directly to the sensor electrode. Alternatively or additionally, it is also possible to effect a binding to a surface of a housing inner wall of the detector chamber above the sensor electrode in the interior of the detector chamber. By way of example, at least one intermediate layer can be situated on the sensor electrode, the interior of the detector chamber being separated from the sensor electrode via said at least one intermediate layer, wherein it is possible to effect the link to the surface of said at least one intermediate layer via the spacer.

The spacer is intended to be designed, in particular, to assume at least two positions in which the electrically charged particles are at different distances from the sensor electrode. This means that the at least one spacer is intended to enable a relative movement of the charged particles with respect to the sensor electrode, despite linking. This can include a free mobility, which is the case for example with long-chain spacer molecules, or else only a mobility between two positions or some other limited number of positions in which the charged particles are at different distances from the sensor electrode. By way of example, the spacer can be designed to assume different conformations, that is to say at least two different conformations, wherein in the different conformations the electrically charged particles linked via the spacer are at different distances from the sensor electrode.

The at least one spacer can comprise in particular at least one chain-type molecule. The at least one spacer can be selected in particular from the group consisting of: branched or unbranched aliphatic chains, in particular alkyl chains; branched or unbranched polyether chains; branched or unbranched polyimino chains and/or derivatives of the materials mentioned. The spacer can be in particular charge-neutral, in particular non-polar. However, polar configurations are also possible, in principle.

The detector chamber can accommodate in particular at least one receptor, in particular an immobilized receptor. By way of example, this can involve a receptor immobilized at the sensor electrode directly and/or at a surface of the detector chamber at the sensor electrode. Said receptor can be linked for example chemically at the sensor electrode and/or the surface of the detector chamber at the sensor electrode, wherein, as also in the case of the linking of the spacer, various types of bond are appropriate, in principle, that is to say for example covalent bonds and/or ionic bonds and/or complex bonds. The same also analogously applies to the linking of the optional at least one charged particle to the spacer. The receptor is intended to be designed to bind the analyte, in particular reversibly. This binding can comprise for example at least one complex bond and/or at least one ionic bond and/or at least one electrostatic bond and/or at least one hydrogen bridge bond and/or at least one covalent bond and/or at least one van der Waals bond. Van der Waals forces can likewise occur, but were generally only of secondary importance as a rule in particular owing to their low strength and their high dependence on distance.

The receptor can furthermore also be designed to at least partly bind the detector substance, that is to say to bind the detector substance or a part thereof. In particular, the receptor can be designed to bind the optional electrically charged particles and/or other constituents of the detector substance, for example one or a plurality of competitor molecules, which need not necessarily have a net charge. This binding of the detector substance and/or of part thereof can compete in particular with the binding of the analyte. The binding can preferably in turn take place reversibly.

In particular, the at least one receptor can comprise at least one lectin. In this case, as is generally customary, lectins should be understood to mean chemical substances, in particular complex proteins or glycol proteins, which can bind carbohydrate structures, in particular specifically, in particular glucose, which may be of particular interest for example for medically analytical methods. Such lectins are known from biochemistry, for example, where they can bind, for example specifically, to cells or cell membranes and from there trigger biochemical reactions. Preferably, lectins have no enzymatic activity. In particular, the at least one lectin can be selected from the group of glucose-binding lectins, in particular those lectins which can be used for glucose detection. The group can consist for example of: Concanavalin A (Con A), in particular from the jack bean and/or the sword bean, *Lens culinaris* agglutinin, in particular from the lentil, Pealectin-I (PSA), in particular from the pea.

The detector substance can furthermore comprise at least one competitor. By way of example, said at least one competitor can comprise at least one type of competitor particles and/or competitor molecules. Said at least one competitor can also be wholly or partly identical to the electrically charged particle or can comprise at least one other type of particle. The competitor is intended to be designed to bind to the receptor, in particular reversibly. The analyte can comprise in particular at least one polyalcohol and/or at least one sugar, in particular glucose, wherein the competitor likewise comprises at least one sugar, in particular a molecule labeled with a sugar, preferably glucose-labeled dextran. By way of example, the analyte to be detected can be glucose, the at least one receptor can be concanavalin-A, and the at least one competitor can be glucose-labeled dextran.

The detector substance can preferably be designed not to convert the analyte, wherein conversion is understood to mean a chemical reaction in which the detector substance is completely or partly altered and/or consumed. This configuration affords the advantage that ageing effects on account of consumption of the detector substance are reduced. Alternatively, however, the detector substance can also comprise at least one detection reagent which is designed to react with the analyte, that is to say to convert the analyte. By way of example, the detection reagent can comprise at least one enzyme, in particular an enzyme which is designed to oxidize and/or reduce the analyte. However, other types of enzymes can also be used, in principle. In particular, the at least one enzyme can be selected from the groups of enzymes which convert glucose, such as, for example, glucose oxidase (GOD), glucose dehydrogenases, in particular NAD+ dependent and/or PQQ dependent (GlucDOR) and/or FAD dependent GlucDH.

The detection reagent can be designed in particular to influence a pH value within the detector chamber, wherein the detector substance comprises at least one pH-sensitive indicator, wherein the pH-sensitive indicator is designed to change at least one property depending on the pH value, wherein the at least one property is designed to influence the at least one electrical property of the electrical sensor. By way of example, the at least one property of the pH-sensitive indicator can be a pH-dependent structure change and/or a pH-dependent swelling state of the at least one indicator and/or an average charge carrier density of the pH-sensitive indicator and/or a dielectric constant of the pH-sensitive indicator and/or a dipole moment of the pH-sensitive indicator. However, other properties can also be changed depending on the pH value and thereby in turn influence the at least one electrical property of the electrical sensor. The pH-sensitive indicator can comprise a polyanion, preferably a polyacrylic acid and/or a derivative of polyacrylic acid, e.g. polymethacrylic acid. The anionic groups thereof are protoniated as the pH value rises, and are thus, at least partly, neutralized, whereby for example a charged polymer originally stretched in a charge-governed manner becomes entangled. The pH-sensitive indicator can in particular alternatively or additionally comprise at least one swellable material, in particular at least one crosslinked polyelectrolyte. This can be a polyionic molecule, preferably at least one polyanionic polymer, preferably a hydrogel on the basis of polyacrylic acid or a derivative of polyacrylic acid, e.g. polymethacrylic acid. Here the swelling of a hydrogel generally increases as the pH increases, that is to say during its deprotonation, and decreases with increasing protonation. By way of example, at least two possibilities can occur in the case of the pH-sensitive indicator, for example a pH-sensitive reagent. In a first possibility, by way of example, a longitudinal stretching of a polyanion, in particular on account of a repulsion of negative charges in the polyanion, can experience for example a structure change in the form of an entanglement, in particular if, by way of example, the pH value decreases and/or the stretched polyanion is discharged by protonation. In a second possibility, by way of example, a swelling of a three-dimensional, for example water-absorbent, polymer, for example of a hydrogen, can occur owing to a change in the pH value. In this case, the protonation leads to H bonds between anionic groups, as a result of which the latter draw together, in particular, that is to say that the swelling preferably takes place during deprotonation. If, by way of example, in the case of the first possibility and/or the second possibility, a glucose oxidase (GOD) is docked to the polymer or at least generally localized there, said GOD can convert the analyte, in particular the glucose. In this case, the pH value is generally reduced, protons generally arising as reaction product. The polymer is generally protonated, wherein in particular the above-described first possibility or the second possibility can occur as consequences.

Further possible configurations of the invention relate to possible configurations of the electrical sensor. In this regard, the at least one electrical sensor, it also being possible to combine a plurality of electrical sensors of identical or different type, can comprise in particular at least one field effect transistor. In this case, a field effect transistor should be understood to mean a component which comprises at least one first electrode (source electrode), at least one second electrode (drain electrode) and at least one inorganic and/or organic semiconductor, for example as channel, connecting said electrodes and which furthermore comprises at least one gate electrode which is preferably insulated, in particular electrically insulated, from the drain electrode and/or the source electrode and/or the channel, and which influences a charge transport between the source electrode and the drain electrode by means of a field effect.

If the electrical sensor comprises at least one field effect transistor, then the sensor electrode can comprise in particular at least one gate electrode of the field effect transistor. In this case, as explained above, a gate electrode is understood to mean an electrode in the sense of the present invention which is designed to control a current flow between two electrodes (source electrode and drain electrode) through a semiconductor of organic and/or inorganic nature by means of field effects. However, the term gate electrode should be interpreted broadly in this case and can encompass, in principle, any desired integral or multipartitate element which can influence a charge transport in the semiconductor by means of a field effect. In this case, the at least one electrical property of the electrical sensor which is influenced by the detector substance and/or the interaction thereof with the analyte can comprise in particular at least one electrode potential of the gate electrode. In other words, in this configuration the sensor device can be designed in such a way that the field effect of the field effect transistor is influenced by means of the detector substance and the interaction thereof with the analyte in the detector chamber.

The field effect transistor can comprise at least one electrically conductive or semiconducting organic material. In this case, an electrically conductive or semiconducting organic material should be understood to mean a material which is designed to ensure a charge carrier transport through said material. Organic materials of this type are in particular organic materials having an extended π-electron system, in particular organic materials having a multiplicity of conjugated double bonds. In this case, the charge carriers can be contained intrinsically in the organic material or can be injected into the organic material from outside. Therefore, in general it is difficult to differentiate between insulators, semiconductors and conductors in the case of organic materials generally according to classical inorganic standards, and so generally with regard to organic materials reference is made to conductors or semiconductors if they enable current transport. The field effect transistor can therefore be an organic field effect transistor.

This can involve a component which is constructed completely from organic materials and contains, besides organic materials, no inorganic materials, at least as independent component parts or layers. Alternatively, however, the organic field effect transistor can also comprise individual or a plurality of inorganic component parts or layers, provided that at least one organic semiconductor or conductor layer is provided. However, an organic semiconductor or conductor layer, the current flow of which can be influenced by the field effects of the gate electrode, should be provided at least between the source electrode and the drain electrode. However, the source electrode and/or drain electrode can individually or both consist of organic or inorganic conductor materials. The gate electrode, too, if it is configured (see the definition above) as an independent component part, can comprise organic or else inorganic materials. As an alternative to the proposed use of an organic field effect transistor which preferably comprises at least one organic conductor or semiconductor, however, in principle classical inorganic semiconductors can also be used in the context of the present invention.

The field effect transistor can be in particular part of an operational amplifier, that is to say of an electronic amplifying component designed to amplify electrical signals, for example electronic signals, in particular voltage and/or current signals. The operational amplifier can have in particular a non-inverting input and an inverting input and/or a differential amplifier, in particular as input circuit. Exemplary embodiments of an operational amplifier will be described in greater detail below. Furthermore, the sensor device can also comprise circuits which can generate differential signals from alternating currents and/or can evaluate them.

In addition to the gate electrode, the electrical sensor can furthermore comprise at least one counterelectrode, which can be constituted as described above. The sensor device can be designed in particular to apply for example at least one electrical potential to the counterelectrode. The detector chamber can be arranged at least partly between the gate electrode and the counterelectrode.

As an alternative or in addition to a field effect transistor, the electrical sensor can also comprise at least one capacitor, for example having a capacitance of at most 100 pF, in particular at most 10 pF, for example a capacitance of 2 pF, in particular of at most 10 pF, for example having a capacitance of 0.1 pF to 10 pF, which comprises at least two electrodes, wherein at least one of these electrodes or a part thereof is formed by the at least one sensor electrode. In addition to the sensor electrode, the capacitor can furthermore comprise at least one counterelectrode. The detector chamber can be arranged at least partly between the sensor electrode and the counterelectrode. Preferably, the detector chamber completely fills the interspace between the sensor electrode and the counterelectrode, wherein the detector chamber, in particular the chamber, should preferably be designed such that in particular the sensor electrode and/or the counterelectrode are not conductively short-circuited by the surrounding medium, for example the fluid medium and/or the fluid. By way of example, the sensor electrode and the counterelectrode can be configured as parallel electrodes, that is to say as electrodes whose electrode surfaces are oriented substantially parallel to one another, for example with a deviation from a parallelism of not more than 20°, in particular not more than 10° and particularly preferably not more than 5°. However, other capacitor constructions are also possible in principle, for example concentric constructions, in which for example the sensor electrode and/or the counterelectrode are/is configured as ring-shaped electrodes and/or as bar-shaped or wire-shaped electrodes. In turn, as will be described in greater detail below by way of example, cylindrical constructions are also possible, in which the sensor electrode and/or the counterelectrode are applied on a lateral surface of the cylinder, for example by virtue of the detector chamber itself being embodied in a cylindrical fashion, wherein for example the sensor electrode and the counterelectrode are arranged on mutually opposite segments of the lateral surface of the cylinder. Various configurations are possible.

If the electrical sensor is configured as a capacitor or if said electrical sensor comprises at least one capacitor, with the sensor electrode as capacitor electrode, then the at least one electrical property can comprise, in principle, any desired property of the capacitor. In particular, the at least one property can be selected from the group consisting of: a capacitance of the capacitor; a dielectric constant of a medium in the detector chamber; an electrode spacing of the electrodes of the capacitor. Combinations of the properties mentioned and/or other properties can also be used, or else other properties of the capacitor.

The sensor device can furthermore comprise at least one driving unit and/or part of a driving unit. The driving unit can be designed to detect the at least one electrical property of the electrical sensor. By way of example, said at least one driving unit can be completely or partly integrated into the electrical sensor. Alternatively or additionally, however, said driving unit can also be arranged independently of the at least one electrical sensor, for example outside the electrical sensor. While the electrical sensor is preferably configured such that it is completely or at least partly implantable, the driving unit can remain for example completely or partially outside the body tissue. Preferably, however, the driving unit is connected to the electrical sensor, for example in a wired manner. This connection can be configured as permanent or else releasable. The at least one driving unit can comprise for example at least one electrical circuit in order to detect the at least one electrical property of the electrical sensor. By way of example, for this purpose the driving unit can comprise at least one applying device which is designed to apply a current and/or a voltage to the electrical sensor. In this case, DC voltages, DC currents or else AC voltages or AC currents can be used. The driving unit can be adapted to the type of electrical sensor, it also being possible to provide a plurality of electrical sensors. In this regard, the applying device in the case of a field effect transistor, for example, can be designed to apply the at least one voltage and/or the at least one current to the source and/or drain electrode. If the electrical sensor is configured completely or partially as a capacitor, then a current and/or voltage can likewise be applied to the capacitor electrodes. Furthermore, alternatively or additionally, the at least one driving unit can comprise at least one measuring device, for example at least one voltage measuring device, for example at least one AC voltage measuring device and/or at least one DC voltage measuring device, and/or at least one current measuring device, for example at least one AC current measuring device and/or at least one DC current measuring device, for example in order to detect a current through one or a plurality of leads to the electrical sensor. Alternatively or additionally, one or a plurality of voltage measuring devices can be provided, for example in order to detect a voltage between at least two measurement points of the electrical sensor, for example a voltage between two electrodes of the electrical sensor, for example a voltage between two capacitor electrodes of a capacitor and/or a voltage between a source electrode and a drain electrode and/or other electrodes of a field effect transistor. Further configurations of the driving unit are also possible. In this regard, the driving unit, by way of example, as will be explained in even more greater detail below, can implement at least one oscillator and/or be implemented for example with at least one capacitive bridge circuit.

The driving unit can be configured for example with one or a plurality of discrete electrical components. Alternatively or additionally, however, the driving unit can also be configured wholly or partly as an integrated circuit, for example as an application-specific integrated circuit (ASIC). The driving unit can comprise in particular at least one wired or wireless interface in order to output at least one signal to a further device, for example to at least one reader, which will be described in greater detail below.

The driving unit can be designed in particular to generate at least one signal, and optionally to forward said signal for example via at least one interface, in particular at least one periodic signal, having one or a plurality of frequencies or a frequency band. For this purpose, the driving unit can comprise for example at least one oscillator. The driving unit and the electrical sensor can be designed in particular in such a way that the signal can be varied by the analyte concentration. By way of example, this can take place in the form of an influencing of a frequency of the signal. The frequency can be for example a carrier frequency, for example a carrier frequency of a radio frequency directly, and/or an amplitude and/or a phase. The influencing of the frequency can be for example a frequency modulation, for example if the frequency is a function of a glucose concentration and/or an amplitude modulation and/or a phase modulation. In this way, for example by means of a reader, the analyte concentration in the fluid and/or the detector chamber can be deduced directly or indirectly from the influencing of the signal, for example from a frequency shift and/or some other type of frequency change and/or from a phase change, for example as information in a phase angle. Such influences on a signal are possible for example by virtue of the fact, as will be explained in even greater detail below, that the electrical sensor and/or part thereof, for example a capacitor, are/is incorporated into a resonant circuit and/or into an oscillator circuit, such that the at least one electrical property of the electrical sensor directly affects the oscillation properties of the oscillator and/or of the resonant circuit and/or directly affects a phase-locked loop (PLL).

The driving unit can be designed in particular to apply at least one voltage sequence and/or at least one current sequence to the electrical sensor and preferably to detect at least one frequency response of the electrical sensor. The voltage sequence and/or the current sequence can comprise for example a temporally periodic signal and/or a succession of signal pulses and/or a stepped signal profile. By way of example, the same voltage sequence and/or current sequence can be applied to the entire electrical sensor; in principle, different voltage sequences and/or current sequences can also be applied to individual components of the electrical sensor. The frequency response can be for example an electric current and/or an electrical voltage and/or a frequency. The frequency response can also comprise a plurality of frequencies, in particular a frequency spectrum.

The driving unit and/or electronic components can be encapsulated in particular in relation to the fluid. Furthermore, the driving unit and/or electronic components can also be encapsulated in relation to the fluid medium. An encapsulation can be understood to mean, in particular, avoiding or preventing a contact, in particular an electrical contact; in particular, an encapsulation can be understood to mean a constituent of the sensor device which can serve for the purpose of encapsulation. An encapsulation of the driving unit can form at least part of the housing of the detector chamber. The encapsulation can preferably be configured in such a way that the fluid and/or the fluid medium and/or the detector substance cannot cause an electrical short circuit. In this case, a short circuit can be understood to mean in particular an electrical resistance of less than $10^9$ ohms. In particular, the encapsulation can be configured in such a way that no short circuit on account of the fluid and/or the fluid medium and/or the detector substance can arise between the electrodes of the electrical sensor and/or between the electrodes of the compensation sensor and/or between components of the driving unit and/or components of the bridge circuit.

As explained above, in the context of the present invention it is particularly preferred if the electrical sensor, in particular the sensor electrode, comprises at least one organic conductive or semiconducting material. As explained above, this is intended to involve an organic material which is designed to support a current transport. Such organic conducting or semiconducting materials are known in principle to the person skilled in the art. What is advantageous about the use of organic conductive and/or semiconducting materials is, in particular, that the latter do not require complex inorganic semiconductor processes, which might possibly not be compatible technically with wet-chemical or other chemical processes for producing the sensor device, in particular with the detector chamber and the detector substance.

The integration of at least one organic conductive or semiconducting material, in particular an organic conductive or semiconducting polymer, can take place in various ways. By way of example, the electrical sensor can comprise a layer construction. As described above, the sensor electrode can comprise for example only a surface of the electrical sensor or can also comprise one or a plurality of layers. If the at least one sensor electrode comprises one or a plurality of electrode layers, then the latter can be for example organic and/or inorganic in nature, wherein combinations, that is to say hybrids, are also possible. By way of example, in the case of an organic field effect transistor, a layer construction is possible in which at least one organic conductor and/or semiconductor is provided, for example at least one conducting or semiconducting polymer. It is possible to apply to the latter at least one electrode layer of organic and/or inorganic nature, or the surface of the organic conductor or semiconductor can itself function as sensor electrode. By way of example, at least one conductive polymer, for example on the basis of polyalanine or on the basis of polythiophenes, for example PEDOT/PSS, can serve as organic electrode layer. Optionally, at least one inorganic electrode layer can be provided, for example a metallic electrode layer. Analogous constructions are also possible, in principle, if the electrical sensor comprises at least one capacitor. In this case, too, the at least one sensor electrode can be configured as a capacitor electrode of organic and/or inorganic nature, wherein it is particularly preferred if said at least one sensor electrode comprises at least one conductive or semiconducting organic material, for example at least one organic conductive or semiconducting polymer.

If at least one organic conductive or semiconducting material is used in the context of the at least one electrical sensor, in particular for the at least one sensor electrode, then said material can be configured, in principle, in various ways which are known in principle to the person skilled in the art. It is particularly preferred if the organic conductive or semiconducting material, in particular for the at least one sensor electrode, but also possibly for other elements of the electrical sensor, comprises at least one material selected from the conjugated polymer, in particular a conjugated polymer from the group consisting of a polythiophene, a polyphenylenevinylene, a polyaniline, a polysulfonic acid, a fluorene, a polyacetylene, a polyparaphenylene, a polyazulene, a polyparaphenylene sulfide, a polypyrrole, a polycarbazole, a polydiaminophthalene and/or derivatives thereof, that is to say for example derivatives in which substitutions are effected, and an organic monomer or oligomer having a conjugated double bond system, in particular a monomer selected from the group consisting of anthracene, pentacene and a triphenylamine and derivatives thereof.

As described above, the sensor electrode can allocate and/or be assigned in particular to the detector chamber and/or be arranged in the detector chamber and/or else be wholly or partly identical to the detector chamber in terms of component parts, such that said sensor electrode is accessible from the detector chamber and/or can preferably be electrically influenced by the detector chamber. Alternatively or additionally, however, the at least one sensor electrode can also be arranged outside the detector chamber, such that at least one spacer can be provided for example between the detector chamber and the sensor electrode. In particular, the at least one spacer can comprise at least one spacer layer. By way of example, at least one electrically insulating spacer layer can be provided, preferably at least one layer of an organic insulator.

As described above, it is particularly preferred if the sensor device is completely or partly implantable to a body tissue of a user. It is particularly preferred if the electrical sensor is configured at least partly as an elongated sensor, wherein the elongated sensor comprises at least the detector chamber or a part thereof and preferably the sensor electrode. The elongated sensor can be designed in particular for being inserted at least partly into a body tissue of a user. In this case, an elongated sensor should be understood to mean a sensor which has a longitudinal extent which exceeds its lateral extent by at least by a factor of 2, preferably by at least a factor of 5 and particularly preferably by at least a factor of 10. By way of example the elongated sensor can have a maximum lateral extent, perpendicularly or transversely with respect to the longitudinal extent, which does not exceed 7 mm, preferably does not exceed 5 mm and particularly preferably does not exceed 3 mm or even does not exceed 2 mm. The advantage in particular of organic layer constructions can be seen in the fact that they can be made extremely thin, for example in a range of less than 1 µm, in particular in a range of less than 500 nm and for example even in the Angstrom range.

It is particularly preferred if the elongated sensor, in particular the sensor device or at least part of the sensor device, is configured at least partly flexible and/or pliable, such that it is bendable for example about an axis transversely with respect to the longitudinal extent, for example an axis parallel to a layer construction of the elongated sensor, for example under customary forces occurring in an inserted state in the body tissue, for example forces of 5-10 N, such that for example it is possible to deflect ends of the elongated sensor relative to one another by at least 100 micrometers, in particular by at least 500 micrometers or even by at least one 1 mm, under said forces. Such flexibility, which can include elasticity properties and/or plastic properties, can likewise easily be ensured by organic layer constructions since the latter can readily be configured as flexible, for example by corresponding substrates being chosen. In this regard, by way of example, the preferred capacitor described above and/or the preferred field effect transistor described above, both components in particular as organic components, can comprise at least one substrate material, for example a glass material and/or a plastics material, to which one or a plurality of layers, for example one or a plurality of organic layers are applied. Said substrate material can be made extremely thin for example with a thickness of less than 500 µm, in particular of less than 100 µm, and can accordingly have flexible properties.

The elongated sensor can have in particular a shape selected from the group consisting of a strip shape and a bar shape, in particular a bar shape having a round cross section. In this case, a bar shape should be understood to mean a cylindrical shape. As described above, the elongated sensor in the case of a cylindrical shape can have in particular a concentric construction and/or a construction having electrodes on lateral surfaces.

As described above, the sensor device can have in particular at least one interface. The sensor device can be designed to communicate with a reader via the at least one interface, in particular via at least one wireless interface, for example a radio interface and/or a capacitive interface, in particular via at least one transponder. This configuration is also particularly preferred in the case of an implantable sensor.

The sensor device can be designed in particular to draw energy from an environment, in particular a body tissue, in particular by means of so-called energy harvesting. This configuration is also particularly preferred in the case of an at least partly implantable electrical sensor, for example the elongated sensor described above. In this case, energy harvesting should be understood to mean a process in which in principle arbitrary forms of energy in an environment are used for obtaining energy, for example without the need to deliberately provide an energy store and/or energy supply, which can nevertheless be provided within the sensor system, in particular within the electrical sensor and/or within the elongated sensor. In this regard, by way of example, energy can be obtained from temperature differences with respect to the environment. Alternatively or additionally, it is possible to use for example vibration effects and/or acceleration forces, for example by means of corresponding piezoelectric devices. In turn alternatively or additionally, for example electrochemical processes can be used to obtain energy from the environment. Such processes of energy harvesting are known in principle to the person skilled in the art. As an alternative or in addition to a unit for energy harvesting, however, as described above, the sensor device can have at least one internal or external energy supply. By way of example, at least one electrical energy store can be provided within the sensor device, in particular within the electrical sensor and/or a driving unit, for example at least one capacitor, in particular a supercap, at least one battery and/or at least one rechargeable battery. In turn alternatively or additionally, energy can also be introduced from outside, for example for the purpose of storage and/or direct use, for example by said energy being radiated in from outside. Various possibilities for the energy supply are provided.

A further aspect of the present invention comprises a sensor system. Said sensor comprises at least one sensor device in accordance with one or a plurality of the configurations described above. Furthermore, the sensor system comprises at least one reader. The sensor device and the reader are intended to be designed to communicate with one another, in particular wirelessly, for example via a capacitive interface and/or an inductive interface and/or an interface for exchanging electromagnetic signals, for example a radio interface. The signals can be exchanged unidirectionally in one of the two directions or else bidirectionally. A reader should generally be understood to mean a device which can communicate with the sensor device. Furthermore, the reader can include further functions. By way of example, the reader can comprise at least one driving and/or evaluation device in order to drive the sensor device for at least one measurement of an analyte concentration and/or in order to receive one or a plurality of signals of the sensor device and to evaluate said signal(s) completely or partly. By way of example, for this purpose the reader can comprise at least microcontroller and/or some other data processing device and/or at least one data storage device. The reader can furthermore comprise at least one user interface in order for example to enable control commands to be input by a user and/or in order to enable information to be output to a user and/or some other device, for example via at least one display, at least one operating element such as, for example, one or a plurality of keys and/or other user interfaces known in principle to the person skilled in the art.

A further aspect of the present invention proposes a method for detecting at least one analyte in a fluid. This method can be carried out in particular using a sensor device in accordance with one or a plurality of the configurations described above, and so, with regard to possible configurations of the method, reference can be made to the above description of the sensor device. The method can be used for the in vitro diagnostics of at least one analyte in a body fluid. Alternatively or additionally, however, the method can also be used for in vivo diagnostics, for example in a body tissue.

At least one closed detector chamber and at least one electrical sensor having at least one sensor electrode are used in the method. The electrical sensor can preferably be electrically influenced by the detector chamber. In the method, the detector chamber is connected to the fluid in such a way that the analyte penetrates into the detector chamber. The detector chamber comprises at least one detector substance which influences at least one electrical property of the electrical sensor depending on a concentration of the analyte in the detector chamber.

The sensor device described above, the sensor system described above and the method described above have numerous advantages over known devices, systems and methods.

In particular the optional use of organic conducting and/or semiconducting materials leads to advantages during production and/or use. Organic conducting and/or semiconducting materials can be applied in particular by wet-chemical methods, for example printing processes such as, for example inkjet printing, screen printing, flexographic printing, pad printing or other printing techniques. Alternatively or additionally it is possible to use blade coating techniques, spin coating, roller coating or other wet-chemical techniques. In turn alternatively or additionally it is possible to use a deposition from the vapor phase, for example physical deposition methods such as vapor deposition and/or sputtering, and/or chemical vapor deposition methods. Deposition from the liquid phase can be effected from solutions, emulsions or dispersions. In particular using organic conducting and/or semiconducting materials, structural detection processes can be deliberately combined with electrical measurement methods. As a result, the serial processing of diverse chemical reaction sequences can advantageously be avoided, and an electrically utilizable signal can be generated in particular directly in one of the first process stages. If applicable, error sources and/or disturbance sources, such as noise influences, for example, are reduced by signal processing steps being shortened.

In particular, in the context of the present invention, a biogenic analyte, for example a glucose present in a measurement liquid, can act directly on electrically detectable variables and its concentration can be determined with the aid of, for example, affinity interactions, by means of electronic methods.

The sensor device can be configured as multipartite or else integral, wherein in particular even monolithic constructions are possible. In this regard, at least one polymer monolith comprising for example a plurality of or all the different functional stages can be produced for example by the combination of specific modified polymer materials. Said functional stages can be coordinated with one another with regard to their materials and/or their production processes. In particular, parts of the sensor device and/or the entire sensor device can be manufactured inexpensively in a so-called reel-to-reel process.

The analyte detection in the context of the present invention can be configured in particular, as described above, without chemical conversions. This is associated with the advantage that, preferably, consumption of the detector substance and/or parts thereof and/or consumption of the analyte itself do(es) not occur. By way of example, consumption of glucose and the reactants thereof can be avoided in this way. Furthermore, it is possible to avoid the occurrence of reaction products, for example gluconolactone, hydrogen peroxide and/or hydrogen, which, if appropriate, would otherwise have to be discharged from the reaction zone, for example the detector chamber, in order for example to avoid a rupture of the detector chamber and/or adverse influencing of the detector chamber by gaseous products. The detection of the analyte preferably proceeds via the setting of a distribution equilibrium dependent only on the analyte concentration. Said equilibrium and its concentration-dependent dynamic range can be registered, via the above-described at least one electrical property of the electrical sensor.

By way of example, an analyte to be detected can occupy statistically and preferably reversibly, in particular in a temporally limiting manner, analyte-specific binding sites of a receptor and, if appropriate, release them again. The degree of assignment and/or occupancy, with regard to the temporal dynamic range, is generally then only dependent on the diffusion-governed analyte concentration and the affinities. The sensor device and in particular the detector chamber and/or the detector substance can therefore be designed in particular in such a way that the diagnostically relevant region, in particular the detector chamber, is covered by the ratio of the binding sites to the maximum analyte concentration.

On account of the preferred configuration wherein no consumption of detector substance and/or analyte takes place, the detection process can proceed in vitro theoretically for an unlimited time.

In vivo, temporal limits cannot be predefined by consumption and reaction products, but rather solely by tissue repair measures, for example can be limited by an encapsulation, healing processes or the like, but generally not by sensor-side processes.

Since an equilibrium setting, in particular within the detector chamber, in the absence of analyte, is advantageously reversible, relative calibrations of the proposed sensor device can be carried out, in particular serially, after a defined depletion process has been carried out, followed by a defined concentration establishment. In this regard, by way of example, measured values of a defined reference solution, which are measured in particular in vitro, can be related to an in vivo measured value, without the sensor element becoming unusable as a result of this process, in contrast to conventional test strips, for example.

Since the chemical substances involved, in particular the at least one detector substance, can preferably be configured as electrochemically passive, they can generally operate in quasi-aqueous solution or in aqueous solution, for example in interstitial fluid. In this regard, by way of example, the detector chamber can be filled with a fluid medium which directly corresponds, in terms of its basic composition, to the fluid in which the analyte is to be detected, or which can be established for example chemically similarly thereto, for example by the use of isotonic solutions. In principle, however, the proposed sensor device and the proposed method are also suitable for use in non-liquid fluids, for example in gases.

In particular for use for human beings, it is particularly preferred if the sensor device is configured as completely or partly biocompatible, in particular a part of the sensor device which is insertable into a body tissue, for example the elongated sensor described above. This can be ensured for example by using biocompatible materials, for example biocompatible organic materials. Alternatively or additionally, however, the sensor device can also be provided completely or partly with an encapsulation, for example a protective sheath, which is biocompatible and which is designed for example to prevent substances of the sensor device from emerging into the surrounding body tissue and/or reactions of the body tissue with the sensor device or parts thereof. The optional encapsulation can be configured as separate from the optional housing of the detector chamber, but can also be wholly or partly integrated into said housing or be embodied jointly therewith. Encapsulations are known in principle to the person skilled in the art from the field of implantable sensor elements. In particular, allergic reactions can be avoided in this way.

Furthermore, the requirements of sterilization can also be taken into consideration in the context of the present invention. In contrast to electrochemical sensors, the sensor devices according to the invention can generally not only be radiation-sterilized but if appropriate also sterilized thermally and/or by chemical methods.

To summarize, in the context of the present invention, the following embodiments are regarded as particularly preferred:

Embodiment 1 sensor device for detecting at least one analyte in a fluid, in particular in a body fluid, comprising at least one closed detector chamber and at least one electrical sensor having at least one sensor electrode, wherein the electrical sensor can preferably be electrically influenced by the detector chamber, wherein the detector chamber can be connected to the fluid in such a way that the analyte can penetrate into the detector chamber, wherein the detector chamber comprises at least one detector substance, wherein the detector substance is designed to influence at least one electrical property of the electrical sensor, in particular at least one electrical property of the sensor electrode, depending on a concentration of the analyte in the detector chamber.

Embodiment 2 sensor device according to one of the preceding embodiments, wherein the detector chamber has at least one membrane, in particular at least one analyte-specific membrane, wherein the membrane is designed to enable the analyte to penetrate into the detector chamber reversibly and preferably to retain the at least one detector substance in the detector chamber.

Embodiment 3 sensor device according to one of the preceding embodiments, wherein the electrical sensor furthermore comprises at least one counterelectrode in addition to the sensor electrode, wherein the sensor device is designed to apply at least one electrical potential to the counterelectrode.

Embodiment 4 sensor device according to the preceding embodiment, wherein the detector chamber is at least partly arranged between the sensor electrode and the counterelectrode.

Embodiment 5 sensor device according to one of the preceding embodiments, wherein the sensor device furthermore comprises at least one compensation sensor.

Embodiment 6 sensor device according to the preceding embodiment, wherein the compensation sensor is uninfluenced by the concentration of the analyte in the detector chamber.

Embodiment 7 sensor device according to one of the two preceding embodiments, wherein the compensation sensor is embodied structurally identically to the electrical sensor, with the proviso that the at least one electrical property of the compensation sensor is uninfluenced by the concentration of the analyte in the detector chamber.

Embodiment 8 sensor device according to one of the three preceding embodiments, wherein the compensation sensor comprises at least one compensation sensor electrode, wherein the detector substance is connected to the sensor electrode, wherein the compensation electrode is free of the detector substance.

Embodiment 9 sensor device according to one of the four preceding embodiments, wherein the electrical sensor and the compensation sensor are incorporated into an electrical bridge circuit.

Embodiment 10 sensor device according to one of the preceding embodiments, wherein the detector substance comprises electrically charged particles, in particular electrically charged particles and/or charged molecules.

Embodiment 11 sensor device according to the preceding embodiment, wherein the detector chamber and the detector substance are configured in such a way that an average distance between the electrically charged particles and the sensor electrode and/or a charge distribution within the detector chamber are dependent on a concentration of the analyte in the detector chamber.

Embodiment 12 sensor device according to the preceding embodiment, wherein the detector chamber and the detector substance are configured in such a way that the average distance between the electrically charged particles and the sensor electrode and/or the charge distribution within the detector chamber change(s) reversibly in the event of a change in the concentration of the analyte in the detector chamber.

Embodiment 13 sensor device according to one of the two preceding embodiments, wherein the detector chamber and the detector substance are configured in such a way that layer formation of at least two layers having different electrical charges takes place within the detector chamber, wherein the distribution of the layers and/or the distance thereof from the sensor electrode are/is dependent on the concentration of the analyte in the detector chamber.

Embodiment 14 sensor device according to one of the four preceding embodiments, wherein the detector substance furthermore comprises at least one spacer, wherein the spacer is designed to bind the electrically charged particles to the sensor electrode and/or a surface of the detector chamber at the sensor electrode, wherein the spacer is designed to assume at least two positions in which the electrically charged particles are at different distances from the sensor electrode.

Embodiment 15 sensor device according to one of the preceding embodiments, wherein the detector substance is configured in such a way that dielectric properties of the detector substance are dependent on a concentration of the analyte in the detector chamber.

Embodiment 16 sensor device according to one of the preceding embodiments, wherein the detector chamber accommodates at least one receptor, in particular an immobilized receptor, preferably a receptor immobilized at the sensor electrode and/or a surface of the detector chamber at the sensor electrode, wherein the receptor is designed to bind the analyte, in particular reversibly.

Embodiment 17 sensor device according to the preceding embodiment, wherein the detector substance furthermore comprises at least one competitor, wherein the competitor is designed to bind to the receptor, in particular reversibly, wherein the analyte comprises in particular a sugar, in particular glucose, wherein the competitor preferably likewise comprises at least one sugar, in particular a molecule labeled with a sugar, preferably a glucose-labeled dextran.

Embodiment 18 sensor device according to one of the preceding embodiments, wherein the detector substance comprises at least one detection reagent, wherein the detection reagent is designed to react with the analyte, in particular at least one enzyme.

Embodiment 19 sensor device according to the preceding embodiment, wherein the detection reagent is designed to influence a pH value within the detector chamber, wherein the detector substance comprises at least one pH-sensitive indicator, wherein the pH-sensitive indicator is designed to change at least one property depending on the pH value, wherein the at least one property is designed to influence the at least one electrical property of the electrical sensor.

Embodiment 20 sensor device according to one of the preceding embodiments, wherein the electrical sensor comprises at least one field effect transistor, in particular an organic field effect transistor, wherein the sensor electrode comprises at least one gate electrode of the field effect transistor.

Embodiment 21 sensor device according to the preceding embodiment, wherein the field effect transistor is part of an operational amplifier.

Embodiment 22 sensor device according to one of the two preceding embodiments, wherein, in addition to the gate electrode, the electrical sensor furthermore comprises at least one counterelectrode, wherein the sensor device is designed to apply at least one electrical potential to the counterelectrode, wherein the detector chamber is at least partly arranged between the gate electrode and the counterelectrode.

Embodiment 23 sensor device according to one of the preceding embodiments, wherein the electrical sensor comprises at least one capacitor, wherein, in addition to the sensor electrode, the capacitor furthermore comprises at least one counterelectrode, wherein the detector chamber is at least partly arranged between the sensor electrode and the counterelectrode.

Embodiment 24 sensor device according to the preceding embodiment, wherein the sensor device is designed to apply at least one electrical potential to the counterelectrode.

Embodiment 25 sensor device according to one of the preceding embodiments, wherein the sensor device furthermore comprises at least one driving unit, wherein the driving unit is designed to detect the at least one electrical property of the electrical sensor.

Embodiment 26 sensor device according to the preceding embodiment, wherein the driving unit is designed to generate at least one signal, in particular at least one periodic signal, wherein the driving unit and the electrical sensor are designed in such a way that the signal can be varied by the analyte concentration, in particular by an influencing of a frequency of the signal.

Embodiment 27 sensor device according to one of the two preceding embodiments, wherein the driving unit is designed to apply at least one voltage sequence and/or at least one current sequence to the electrical sensor and preferably to detect at least one frequency response of the electrical sensor.

Embodiment 28 sensor device according to one of the three preceding embodiments, wherein the driving unit is encapsulated relative to the fluid.

Embodiment 29 sensor device according to the preceding embodiment, wherein an encapsulation of the driving unit forms at least part of a housing of the detector chamber.

Embodiment 30 sensor device according to one of the preceding embodiments, wherein the electrical sensor, in particular the sensor electrode, comprises at least one organic conductive or semiconducting material, in particular at least one conductive or semiconducting polymer.

Embodiment 31 sensor device according to one of the preceding embodiments, wherein at least one spacer, in particular at least one spacer layer, in particular an electrically insulating spacer layer, preferably at least one layer of an organic insulator, is arranged between the sensor electrode and the detector chamber.

Embodiment 32 sensor device according to one of the preceding embodiments, wherein the sensor device is designed to communicate with a reader via at least one interface, in particular via at least one wireless interface, in particular via at least one transponder.

Embodiment 33 sensor system, comprising at least one sensor device according to one of the preceding embodiments and at least one reader, wherein the sensor device and the reader are designed to communicate with one another, in particular wirelessly.

Embodiment 34 method for detecting at least one analyte in a fluid, in particular using a sensor device as claimed in any of the preceding claims relating to a sensor device, wherein at least one closed detector chamber and at least one electrical sensor having at least one sensor electrode are used, wherein the electrical sensor can preferably be electrically influenced by the detector chamber, wherein the detector chamber is connected to the fluid in such a way that the analyte penetrates into the detector chamber, wherein the detector chamber comprises at least one detector substance, wherein the detector substance influences at least one electrical property of the electrical sensor depending on a concentration of the analyte in the detector chamber.

BRIEF DESCRIPTION OF THE SEVERAL VIEWS OF THE DRAWINGS

Further details and features of the invention are evident from the following description of preferred exemplary embodiments, in particular in conjunction with the dependent claims. In this case, the respective features can be realized by themselves or as a plurality in combination with one another. The invention is not restricted to the exemplary embodiments. The exemplary embodiments are illustrated schematically in the drawing figures. In this case, identical reference numerals in the individual drawing figures designate elements that are identical or functionally identical or correspond to one another with regard to their functions.

In the Figures, specifically.

Figure 1A:
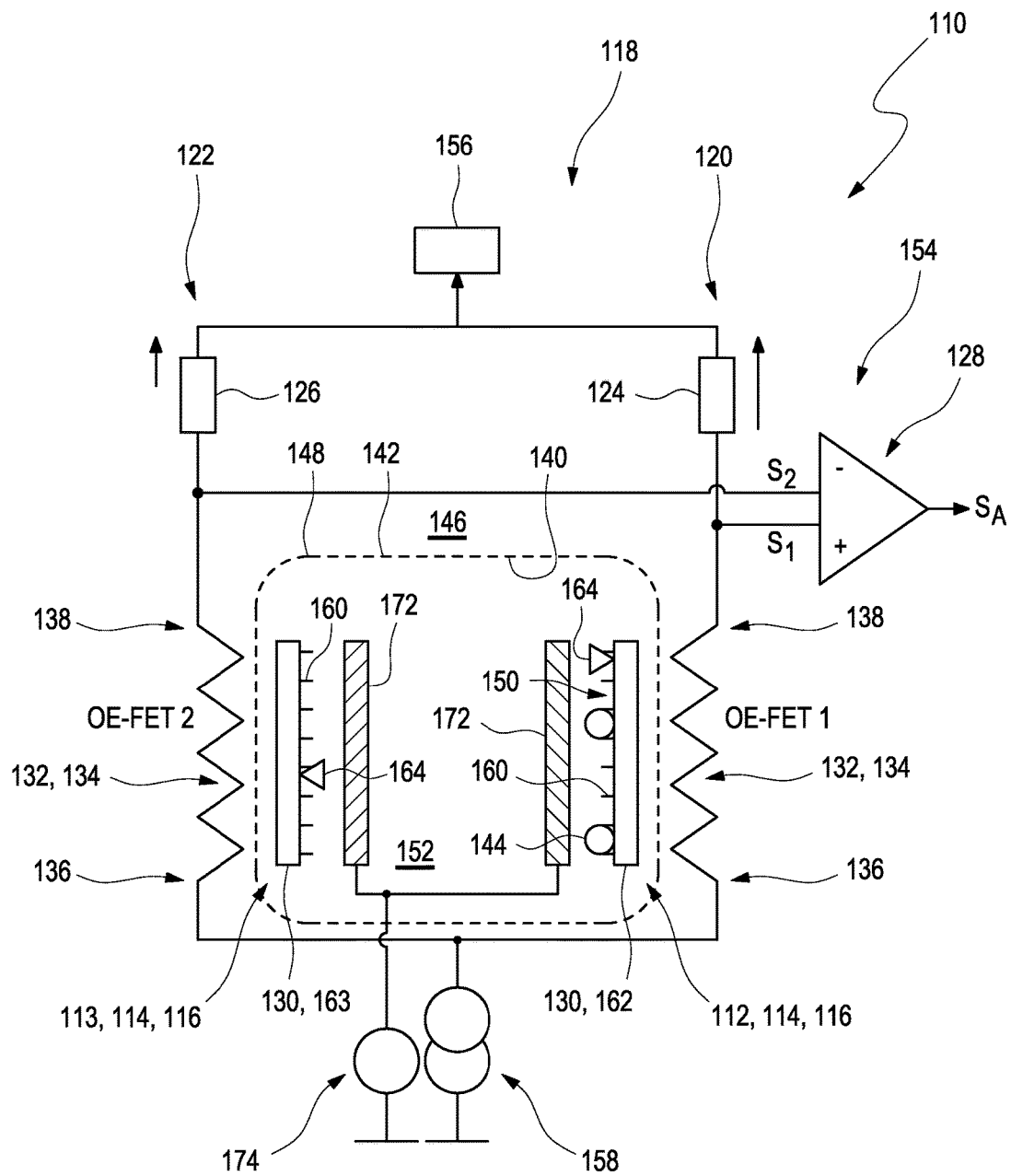
FIG. 1A shows a basic schematic diagram of one example of a sensor device with an operational amplifier.
Figure 1:
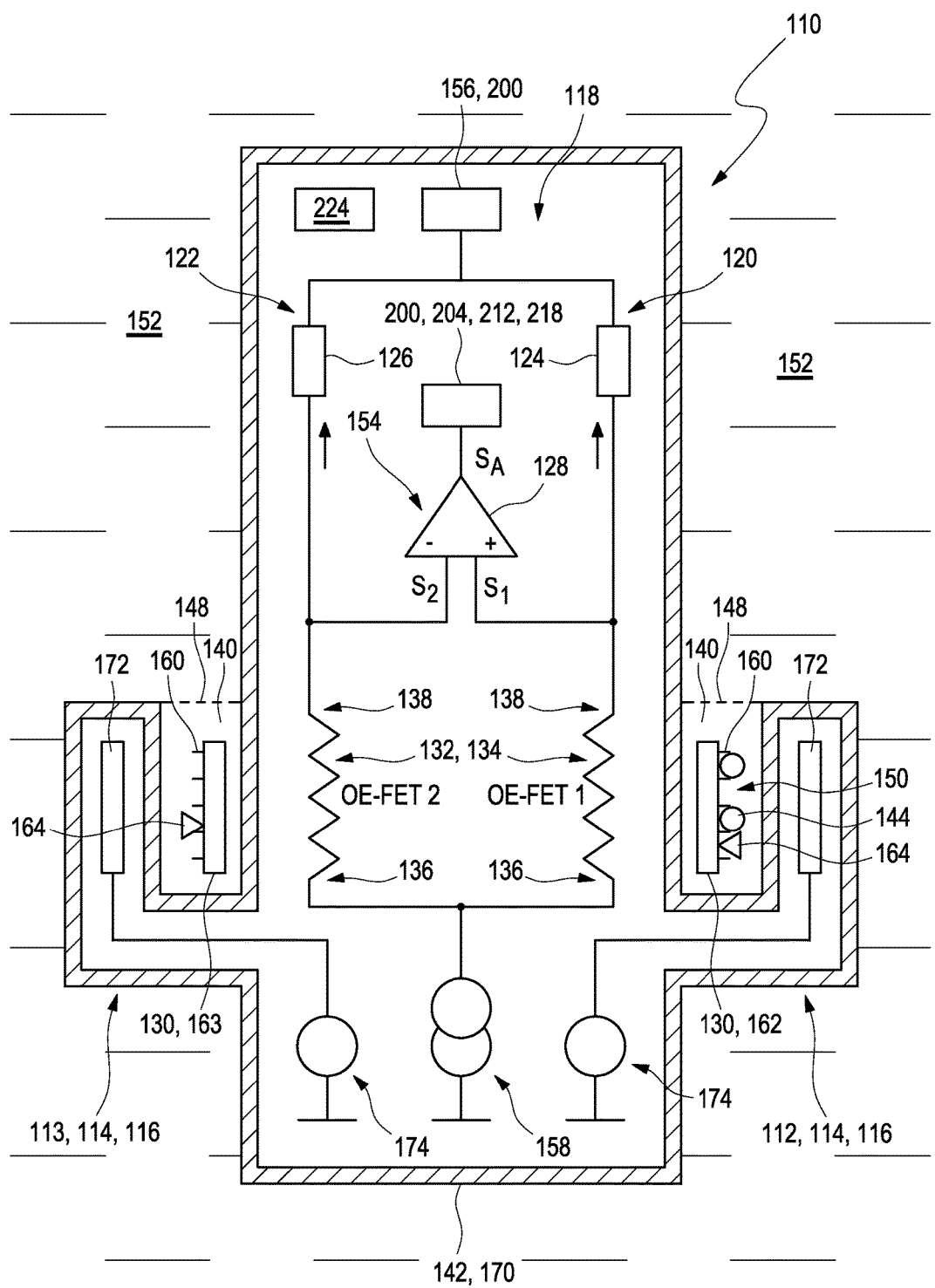
FIG. 1B shows a further example of a sensor device with an operational amplifier.

Skilled artisans will appreciate that elements in the drawings are illustrated for simplicity and clarity and have not necessarily been drawn to scale. For example, the dimensions of some of the elements in the drawing Figs. may be exaggerated relative to other elements to help improve understanding of the embodiments of the present invention.

DETAILED DESCRIPTION OF THE INVENTION

For the purposes of describing and defining the present invention it is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

FIGS. 1A and 1B illustrate, in highly schematic illustration, exemplary embodiments of a sensor device 110 according to the invention which are based on the use of one or a plurality of electrical sensors 112, which in these exemplary embodiments are configured as field effect transistors 114, preferably as organic field effect transistors 116, also designated by OE-FET 1 and OE-FET 2 in FIGS. 1A and 1B. In the exemplary embodiments in accordance with FIGS. 1A and 1B or else in other configurations in the present invention, the sensor devices 110 can in each case comprise at least one electrical sensor 112 having analyte-specific properties and optionally at least one compensation sensor 113, which is at least substantially uninfluenced by an analyte concentration. In FIGS. 1A and 1B, the OE-FET 1 in each case represents the electrical sensor 112, and the OE-FET 2 represents the compensation sensor 113.

With semiconducting or conducting polymers it is already possible nowadays to produce field effect transistors 114, 116 having good digital switching properties. In principle, a field effect transistor 114, 116 constitutes a voltage-controlled resistor and is an element with which analog signals can be processed. In present-day electronics, silicon-based operational amplifiers 118 generally constitute central elements for signal amplification. Figuratively speaking operational amplifiers 118 generally operate according to the principle of a beam balance, wherein a constant current is generally divided between two controllable resistance branches 120, 122. In FIGS. 1A and 1B, by way of example, the sensor device 110 comprises such an operational amplifier 118 having the two resistance branches 120, 122, into which the field effect transistors 114 OE-FET 1 (electrical sensor 112) and OE-FET 2 (compensation sensor 113) are incorporated. Said resistance branches 120, 122 are composed for example of the controllable field effect transistors 114 and fixed resistors 124, 126. As a result of control signals being applied to said field effect transistors 114, the "current balance", which is balanced in the rest state, can be brought out of equilibrium. As a result, the voltage drop across the fixed resistors 124, 126 changes, for example to the same extent. The two voltage drops can be subtracted in a downstream stage (subtracting stage 128) and the result can be amplified further, if appropriate. In conventional operational amplifiers 118, the two controllable inputs form the differential inputs of the operational amplifier 118. If identical signals are present at the differential inputs, the output signal, which is designated by "$S_A$" in FIGS. 1A and 1B, tends toward zero, apart from possible offsets. By contrast, if the input signals deviate from one another, then the difference is amplified.

The controllable field effect transistors 114 are controlled by an electrode potential, a charge or a voltage being applied to so-called gate electrodes 130. The latter act, generally in an insulating manner, on a bulk resistance of a semiconductor 132, in particular organic conductor or semiconductor 134 of the field effect transistors 114 in FIGS. 1A and 1B, which connects a source electrode 136 to a drain electrode 138 of the field effect transistors 114, which, like the organic semiconductor 134 as well, are merely indicated in FIGS. 1A and 1B. If a negative charge is applied to the gate electrode 130, for example, then the resistance path, that is to say the bulk resistance, of the organic semiconductor 134 can be depleted, and, depending on the doping of the organic semiconductor 134 and/or the properties thereof (for example depletion type or enhancement type), the electrical resistance thereof changes.

In the context of the present invention and the present sensor device 110, this charge control and/or voltage control at the gate electrode 130 is not achieved by applying an external voltage source, but rather by, in an analyte-dependent manner, employing electrical charges to the gate electrode 130 and/or removing them therefrom and/or by generally varying a charge distribution within a detector chamber 140. In the case of organic semiconductors 134, it is possible to bring about an influence for example with intrinsic or else by means of external charge carriers, in particular by π-electrons of the organic semiconductors 134, for example of a polymer being influenced.

Accordingly, in these exemplary embodiments, the sensor devices 110 in accordance with FIGS. 1A and 1B comprise the electrical sensor 112 and the compensation sensor 113, in each case in the form of one or a plurality of field effect transistors 114, in particular organic field effect transistors 116, the gate electrodes 130 of which can be influenced by processes within the at least one detector chamber 140. The electrical sensor 112 and the compensation sensor 113 differ in this case, as will be explained in even greater detail below, in terms of whether or not this influencing is dependent on the concentration of the analyte in the fluid medium 152. While the influencing of the gate electrode 130 of the compensation sensor 113, said gate electrode acting as compensation sensor electrode 163, is at least greatly independent of the concentration of the analyte, the electrical properties are influenced in a manner dependent on the concentration of the analyte in the case of the electrical sensor 112 and the gate electrode 130 thereof functioning as sensor electrode 162.

In both exemplary embodiments, the gate electrodes 150 of the electrical sensor 112 and of the compensation sensor 113, said gate electrodes acting as sensor electrode 162 and as compensation sensor electrode 163, respectively, are by way of example arranged in at least one detector chamber 140 and/or connected to at least one detector chamber 140. In this case, the sensor electrode 162 and the compensation electrode 163 can be arranged in and/or at the same detector chamber 140 or else in different detector chambers 140. The at least one detector chamber 140 accommodates at least one fluid medium 152, which is preferably in reversible analyte exchange with a fluid 146 outside the detector chamber 140, for example via at least one membrane 148.

The exemplary embodiments in FIGS. 1A and 1B differ, inter alia, in the configuration of the detector chambers 140. While the exemplary embodiment FIG. 1A only schematically shows the sensor device 110 and the arrangement of the detector chamber 140 and of the fluid 146, FIG. 1B shows an exemplary embodiment in which a driving unit 154 of the sensor device 110 is configured in an encapsulated manner. Generally, sensitive electronic components of the sensor device 110, in particular a driving unit 154 of the sensor device 110, can be configured as encapsulated individually, in groups or altogether relative to the fluid 146 and/or the fluid medium 152. In this regard, FIG. 1A illustrates the fluid 146 only schematically outside the detector chamber 140, such that, for example, an analyte exchange with the fluid medium 152 within the detector chamber 140 can take place.

In this case, however, the fluid 146 preferably does not come directly into contact with electronic components outside the detector chamber 140, for example by virtue of a corresponding encapsulation of said components. In the exemplary embodiment in accordance with FIG. 1B, by contrast, a housing 142 is provided, which, in interaction with the membrane 148, separates an interior space of the housing 142 in which the driving unit 154 is accommodated, the detector chamber 140 with the fluid medium 152 and an external space with the fluid 146 from one another. This separation has the effect that neither the fluid 146 nor the fluid medium 152 can penetrate into the interior space to the driving unit 154. Furthermore, the separation has the effect that an analyte exchange between the fluid 146 and the fluid medium 152 is possible.

The configuration of the detector chamber 140 in the illustration in accordance with FIG. 1B should be understood to be merely by way of example, numerous other configurations also being possible. By way of example, the detector chamber 140, as illustrated in FIG. 1B, can be configured in the form of one or a plurality of depressions, annular gaps, pockets or other cavities which are formed by the housing 142 and which are separated from the external space by the membrane 148. However, other configurations are also possible, in principle.

Furthermore, in the configurations in accordance with FIGS. 1A and 1B, the gate electrodes 130 are in each case arranged by way of example within the detector chamber 140, which likewise need not necessarily be the case, since said gate electrodes 130 should merely be able to be electrically influenced from the detector chamber 140.

In addition to the at least one sensor electrode 162, the electrical sensor 112 in this or else in other exemplary embodiments of the present invention can have at least one counterelectrode 172, which can be electrically contact-connected or else not contact-connected. The counterelectrode 172 can be uninfluenced by the analyte concentration. Likewise, the at least one compensation sensor 113 can also optionally have at least one counterelectrode 172, such that for example in turn, apart from the sensitivity relative to the analyte, the electrical sensor 112 and the compensation sensor 113 can be configured at least substantially structurally identically. The exemplary embodiments in FIGS. 1A and 1B optionally show such configurations with counterelectrodes 172. The counterelectrodes 172 can be arranged for example wholly or partly within or wholly or partly outside the detector chamber 140. In this regard, FIG. 1A shows by way of example a configuration in which the counterelectrodes 172 are arranged within the detector chamber 140, while FIG. 1B shows a configuration in which the counterelectrodes 172 are arranged outside the detector chamber 140, for example in the interior of the housing 142. A different configuration is also possible in each case. In particular, the detector chamber 140 can be arranged wholly or partly between the sensor electrode 162 or the compensation sensor electrode 163 and the respective counterelectrode 172. However, other configurations are also conceivable.

As explained above, at least one driving unit 154 can be provided, which can be wholly or partly encapsulated relative to the fluid 146 and/or the fluid medium 152. The detector chamber 140 is configured for example as a liquid compartment. The detector chamber 140 can have a housing 142, for example, or the housing 142 can, as illustrated in FIG. 1B, for example, form at least part, in particular at least part of a wall, of the detector chamber 140. The housing 142 can be for example completely or partly permeable to an analyte 144 to be detected in a fluid 146 completely or partly surrounding the detector chamber 140, for example by virtue of said housing having one or a plurality of membranes 148. In the exemplary embodiment illustrated in FIG. 1B, the housing 142 is preferably hermetically sealed, in particular completely impermeable to the analyte 144 to be detected and/or the fluid 146 and/or the fluid medium 152, for example in order to prevent a short circuit, in particular between electronic components, for example bridging. In this case, a short circuit can be understood to mean in particular an electrical resistance of less than $10^9$ ohms. This impermeability can be interrupted for example only by the membrane 148, which, as explained above, can ensure an analyte exchange, for example a reversible analyte exchange, between the fluid 146 and the fluid medium 152. As illustrated in FIG. 1B, the housing 142 can surround for example wholly or partly the driving unit 154 and/or the drain electrode 138 and/or the source electrode 136 and/or the semiconductor 132 and/or the counterelectrode 172 and/or a compensation sensor 113 and/or the electrical sensor 112. By way of example, the housing 142 and/or the detector chamber 140 and/or part thereof can have at least one membrane 148 which is permeable to the analyte 144, but which is designed to retain constituents of a detector substance 150, which is merely indicated in FIG. 1B, in the detector chamber 140. The detector chamber 140 can be filled for example completely or partly with a fluid medium 152, for example a fluid medium 152 which can be identical to the fluid 146 and/or which can be configured as chemically similar to the fluid 146. The gate electrode 130 should preferably be insulated, in particular isolated at high impedance, from the source electrode 136 and/or the gate electrode 130 and/or preferably biased at a defined potential.

Furthermore, the sensor devices 110 in the exemplary embodiments illustrated in FIGS. 1A and 1B optionally comprise, as explained above, in each case the at least one driving unit 154, which can comprise the resistance branches 120, 122, the subtracting stage 128 and optionally a supply voltage 156 and/or a current source 158, which are merely indicated in FIGS. 1A and 1B. The supply voltage 156 and/or the current source 158 can be connected to the parallel-connected resistance branches 120, 122. The subtracting stage 128 can for example respectively tap off signals S1 and S2 between the field effect transistors 114 and the associated fixed resistors 124 and 126 in the respective resistance branches 120, 122.

The detector chamber 140, as illustrated for example in FIG. 1B, can be configured in various ways. As an alternative or in addition to the configuration with at least one housing 142, the detector chamber 140 can for example also be filled and/or enclosed wholly or partly with a liquid-permeable solid material of a liquid-permeable solid structure, for example with a porous material, for example a porous, liquid-permeable foam. Polyurethanes or other porous foams could be mentioned as examples. Various configurations are possible, wherein preferably the field effect transistor 114 and/or electrical contacts should not be short-circuited, in particular electrically short-circuited, by the fluid 146 and/or the fluid medium 152.

Further possible configurations concern the detector substance 150, which can likewise be configured in various ways. By way of example, the detector chamber 140 can accommodate, for example as part of the detector substance 150, at least one receptor 160 which is designed to bind the analyte 144, for example glucose, in particular reversibly. In the exemplary embodiments illustrated in FIGS. 1A and 1B, said receptor 160 can be arranged for example at the gate electrodes 130 and/or at one of the gate electrodes 130. By way of example, said gate electrode 130 can be occupied by one or a plurality of such receptors 160.

It is particularly preferred if the gate electrodes 130 are configured differently, such that one of said gate electrodes 130, the right-hand one of the gate electrodes 130 in FIGS. 1A and 1B, acts as sensor electrode 162 of the electrical sensor 112. By way of example, exclusively the sensor electrode 162 can be occupied by receptors 160 or the receptors 160 of the gate electrodes 130 can be configured differently, such that for example the gate electrode 130 not configured as sensor electrode 162, the left-hand one of the gate electrodes 130 in FIGS. 1A and 1B, cannot bind molecules or merely binds non-specific molecules 164, independently of whether or not glucose is involved. The left-hand one of the gate electrodes 130 can be operated as compensation sensor electrode 163, in particular, wherein the compensation sensor electrode 163 can be comprised by the compensation sensor 113, in particular. The compensation sensor 113 and/or the compensation sensor electrode 163 can supply in particular at least one reference and/or at least one reference value, for example in order to be used in a method for calibrating and/or for gauging and/or for diagnosing at least one malfunction, in particular in the context of the detecting of the analyte 144. The compensation sensor electrode 113 can preferably compensate for at least one error variable, for example at least one offset and/or a synchronism.

The receptor 160 can be configured for example in such a way that it is linked to the analyte 144, for example glucose, for example like an antigen with respect to the antibody. Moreover for example, M. McAlpine in "Nanotechnology-Enabled Flexible Sensors for Medical Diagnostics", paper at "Organic Electronic Congress", Berlin, 10.27.-29.2008, presented in particular hybrid nanowire sensors and discussed possibilities for coupling peptides as receptor 160 to nanowires, in particular for developing electronic noses. This, too, can be realized in the context of the present invention.

The bonds between receptor 160 and analyte 144, which can be configured in various ways, can be reversible, in particular, and can then preferably be based only on an affinity of the analyte 144 to be detected, for example a molecule to be detected, with respect to the gate surface and/or with respect to the receptor 160. Preferably, no chemical conversion takes place, and no reagent of the detector substance 150 is consumed. On average statistically, therefore, in particular an average charge carrier mobility profile can be formed which, integrated over time, is proportional solely to the analyte concentration. In order to form this integral, the operational amplifier 118, for example, this not being illustrated in FIGS. 1A and 1B, can be coupled or coupled with feedback to a capacitor, whereby a further basic circuit of signal processing, an analog integrator, can arise. The sensor device 110 in these exemplary embodiments or else generally in the context of the invention can therefore also be configured as an integrator or comprise such an integrator.

The average binding site occupancy will have a relatively high non-specific signal offset in both resistance branches 120, that is to say in both channels of the operational amplifier 118, generally as a result of non-specific processes, for example by means of the non-specific molecules 164. As a result of the differential amplification of the operational amplifier 118, however, this offset is generally at least largely compensated for in the device in accordance with FIGS. 1A and 1B since both field effect transistors 114, 116 are preferably situated spatially close together. Preferably, the sensor device 110 in these or else in other exemplary embodiments therefore has, as explained above, at least two field effect transistors 114, preferably at least two organic field effect transistors 116, in particular for example at least one field effect transistor 116 comprised by at least one electrical sensor 112 and at least one field effect transistor 116 comprised by at least one compensation sensor 113. The gate electrodes 130 of the field effect transistors 116 can be arranged for example in or at least one common detector chamber 140 or else in or at separate detector chambers 140 and/or can preferably lie close together, for example at a distance of not more than 5 mm, in particular of not more than 2 mm, particularly preferably of not more than 1 mm or even not more than 500 µm. In this case, the field effect transistors 114, 116 can preferably be identical in terms of their basic structure, but the field effect transistors 114, 116 preferably have different specific properties with regard to the analyte 144. In particular, one of the field effect transistors 114, 116, in particular the field effect transistor 114 comprised by the electrical sensor 112, can have one or a plurality of analyte-specific receptors 116. Furthermore, both field effect transistors 114, 116 can react in the same way to the surrounding medium, for example an interstitium. If the analyte 144 is present, then the analyte-specific field effect transistor 114, 116 will react with its sensor electrodes 162 in particular in contrast to the other field effect transistor 114, which is comprised by the compensation sensor 113, for example, and can have a compensation sensor electrode 163, for example, such that the equilibrium is disturbed in the operational amplifier 118, which in turn becomes apparent in the output signal.

Figure 2:
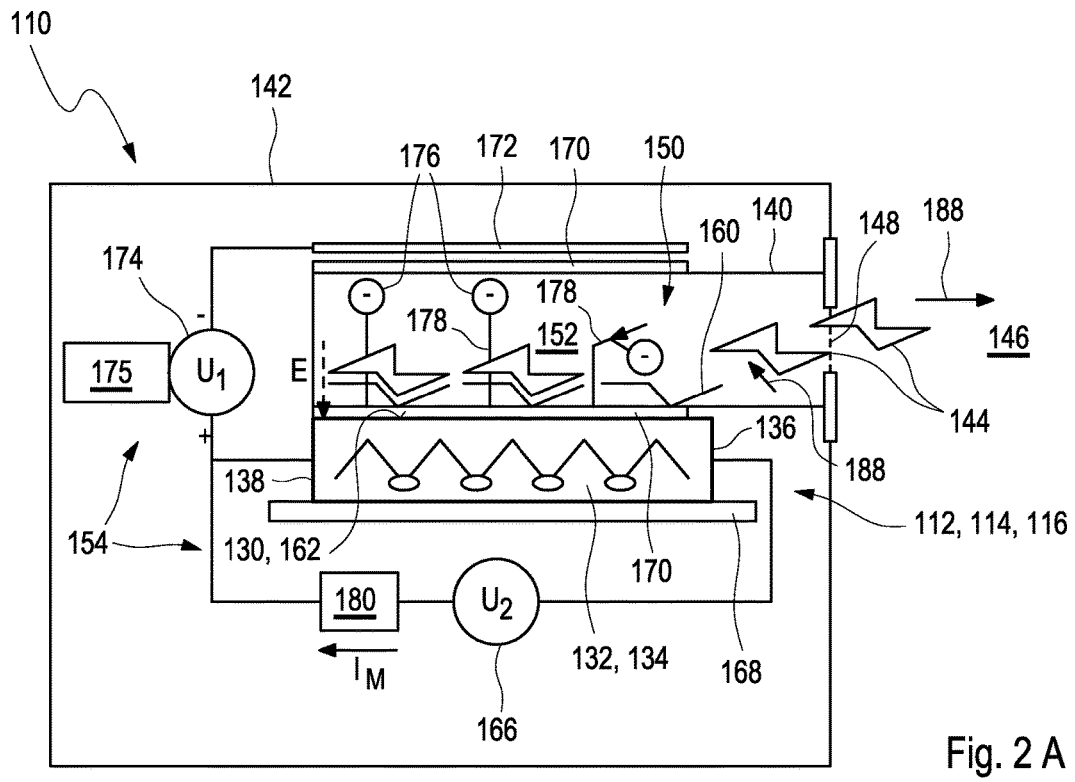
FIGS. 2A and 2B show an exemplary embodiment of a sensor device with a field effect transistor with analyte (FIG. 2A) and without analyte (FIG. 2B)
Figure 2:
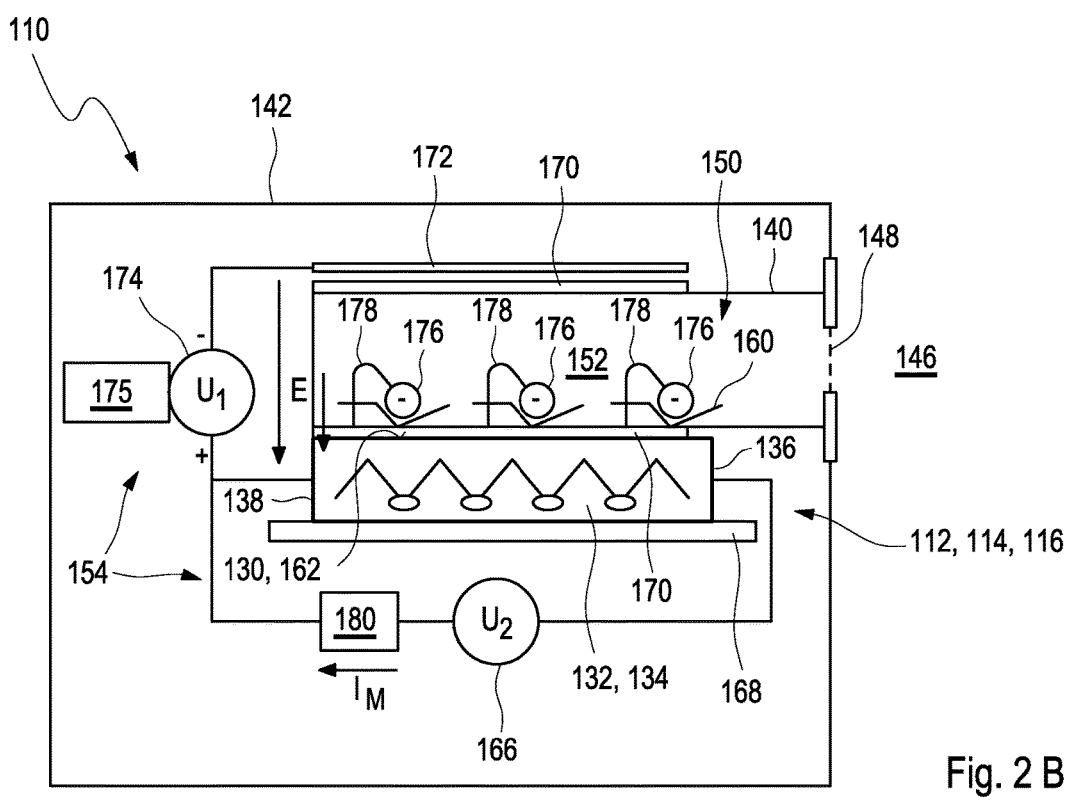

In order that the electrical arrangement is not short-circuited by the fluid medium 152 of the detector chamber 140, for example the interstitium, the bulk resistances between the source electrodes 136 and the drain electrodes 138, in particular the semiconductors 132 or organic semiconductors 134, can be situated outside the detector chamber 140, for example in an insulated manner outside the fluid medium 152, in particular the interstitium. The bulk resistances should preferably be insulated from the gate electrodes 130, wherein a distance between the bulk resistances and the gate electrodes 130 should preferably be chosen to be as small as possible, for example less than 1 µm. Only the gate electrodes 130 can for example be situated within the detector chamber 140 and/or be exposed to the fluid medium 152 within the same. The gate electrodes 130 can then act for example on the bulk resistances of the semiconductors 132 or organic semiconductors 134 by virtue of their electric field forces. One example of short-circuit-free application of gate potentials is illustrated in FIGS. 2A and 2B and will be explained in even greater detail below.

If the field effect transistors 114, 116 in FIGS. 1A and 1B are configured substantially in the same way, then the output signal at the subtracting stage 128 results at least approximately, apart from a possible gain factor, as follows:

$$S_A = S_1 - S_2$$
$$= S_{1analyte} + S_{1offset} - S_{2offset}.$$

with $S_{1offset} \approx S_{2offset}$ it follows therefrom that:

$$S_A \approx S_{1analyte}.$$

In this case, the offsets $S_{1offset}$ and $S_{2offset}$ are generally location-dependent, temperature-dependent, or moisture-dependent or dependent on other parameters. Circuitry arrangements for compensation, in particular of the dependencies mentioned, should be generally known to the person skilled in the art.

The charge carrier mobility and/or conductivity of organic semiconductor materials, for example conductive polymers, are/is generally based on the fact that suitable polymers, for example polythiophene, are present in long molecular chains with extended π-electron systems. By means of the mobile π-electron systems, the π-electrons can move with relatively little energy expenditure along the molecular chains and thus enable a current flow.

FIGS. 2A and 2B show an exemplary embodiment of a sensor device 110 which, in principle, can also be combined with the operational amplifier circuit 118 in accordance with FIGS. 1A and 1B and/or an integrator circuit, but which, in principle, can also be used by itself. By way of example, the right-hand one of the two field effect transistors 114, 116 in FIGS. 1A and 1B, that is to say the field effect transistor 114 having the sensor electrode 162, could be configured in accordance with the exemplary embodiments in FIGS. 2A and 2B. However, a different configuration is also possible, in principle. In this regard, the circuits illustrated in FIGS. 2A and 2B could also be realized in a different way than with the operational amplifier 118 in accordance with FIGS. 1A and 1B. Various combination possibilities are conceivable.

FIGS. 2A and 2B show the exemplary embodiment of the sensor device 110 in different operating states. The sensor device 110 once again comprises an electrical sensor 112, which in this case once again comprises a field effect transistor 114, in particular an organic field effect transistor 116. The field effect transistor 114 once again comprises a semiconductor 132, in particular in the form of an organic semiconductor 134 or organic conductor, for example a conductive polymer, which connects a source electrode 136 and a drain electrode 138 to one another. These electrodes 136, 138 are connected to a voltage source 166 and/or current source 158, for example, and a measurement current $I_M$ flows through said electrodes 136, 138. Said measurement current $I_M$ can be detected for example, in particular via a measuring resistor 180, for example once again with an amplifier circuit and/or affinityoperational amplifier circuit 118, for example analogously to FIGS. 1A and 1B.

The sensor device 110 in accordance with FIGS. 2A and 2B once again has at least one detector chamber 140, for example once again with a housing 142 and/or a medium which is designed to take up a fluid medium 152, for example a porous material, in particular a porous plastics material, which can preferably be enclosed by the housing 142, for example a wholly or partly electrically insulating housing 142. The detector chamber 140 can be embodied for example once again, as shown by way of example in FIGS. 2A and 2B, as a cavity and/or depression in the housing 142. How detector chamber 140 can be necessary, for example, in order for example to insulate the porous material electrically, in particular from electronic components. FIGS. 2A and 2B illustrate by way of example once again an optional membrane 148, for example a glucose-specific, semipermeable membrane 148, which enables glucose to pass through, but which prevents materials of a detector substance 150 from emerging from the detector chamber 140. By means of the glucose-specific membrane 148, for example an equilibrium 188 of analyte 144 can form between the surrounding fluid 146 and an interior of the detector chamber 140. The membrane 148 can be part of the housing 142, for example, and can separate the detector chamber 140 formed in the housing 142 relative to an external space which wholly or partly surrounds the housing 142 and which accommodates the fluid 146, such that an analyte exchange through the medium 148 between the fluid 146 and the fluid medium 152 is possible.

The field effect transistor 114 once again has a sensor electrode 162 in the form of a gate electrode 130 facing the detector chamber 140. By way of example, this can simply involve the surface of the semiconductor 132 or organic semiconductor 134, which, for its part, can be applied on a substrate 168. Alternatively or additionally, at least one additional layer can also be applied on said surface and can then act as gate electrode 130. Furthermore, as indicated in FIGS. 2A and 2B, at least one spacer 170, for example at least one insulating spacer layer 170, can be provided between the gate electrode 130 and the detector chamber 140.

The electrical sensor 112 and/or the compensation sensor 113 optionally in each case comprise at least one counterelectrode 172 by way of example in the optional constructions shown in FIGS. 1A, 1B, 2A and 2B. Said counterelectrode 172 is preferably, but not necessarily, arranged on a side of the detector chamber 140 situated opposite the gate electrode 130, and/or in a different way such that at least part of the detector chamber 140 is arranged between the counterelectrode 172 and the gate electrode 130. The counterelectrode 172 can physically also be regarded as a unit with the gate electrode 130 or as part thereof, since the latter, together with the counterelectrode 172, and if appropriate together with the processes within the detector chamber 140, influences the potential of the gate electrode 130 and thus the electric field within the semiconductor 132.

In the exemplary embodiment illustrated, by way of example a further voltage source 174 is arranged between the counterelectrode 172 and the gate electrode 130, which further voltage source, like the voltage source 166 as well, is to be ascribed to a driving unit 154 of the sensor device 110, and which further voltage source applies a negative potential (−) for example to the counterelectrode 172 and applies a positive electrode potential for example to the drain electrode 138 and, via the latter and the semiconductor 132, 134 or the conductive polymer, to the gate electrode 130. The voltage source 174 can be configured with a changeover switch 175, for example, which switches off the voltage source 174 or else can reverse the priority thereof. Optionally at least one spacer 170, for example at least one insulator layer, can also be provided between the counterelectrode 172 and the fluid medium 152 and/or the detector chamber 140.

The semiconductor 132, in particular the organic semiconductor 134, can be configured for example in such a way that it is applied on the substrate 168. Said substrate 168 can be configured as a passive substrate 168, but in this or in other exemplary embodiments can in principle also comprise one or a plurality of electronic components and/or conductor tracks and/or other electrical or electronic components. In particular, an organic electronic substrate 168 can be involved in this case. Said organic electronic substrate 168 can also comprise for example the terminals for the electrodes 136, 138.

The detector chamber 140 is preferably delimited in a manner electrically insulated from the semiconductor 132 and/or organic semiconductor 134, in particular from the conductive polymer. At the gate electrode 130, which can once again function as sensor electrode 162, electrically charged particles 176 can be provided, for example as part of the detector substance 150. In this case, electrically charged particles 176 should be understood to mean particles which always have a net charge at least under the ambient conditions prevailing in the detector chamber 140, for example in the fluid medium 152. By way of example, charged molecules can be involved in this case. Said charged molecules are permanent charge carriers and are also designated as GM hereinafter. By way of example they can always carry a negative charge, as indicated in FIGS. 2A and 2B.

The electrically charged particles 176 can be restricted in their mobility in particular within the detector chamber 140. By way of example, for this purpose, in the detector chamber 140 at least one spacer 178 can be provided, in particular once again as part of the detector substance 150, said at least one spacer likewise being indicated in FIGS. 2A and 2B. Said spacer 178 can be configured in particular as a mobile spacer. As an alternative or in addition to the use of one or a plurality of spacers 178, suitable other measures can be provided by means of which the electrically charged particles 176 are accommodated in mobile fashion within the detector chamber 140. By way of example, in FIGS. 2A and 2B for illustrating an optionally required localization of the electrically charged particles 176, spacers 178 are provided by means of which the electrically charged particles 176 are mobile in the region of their binding sites, but are immobilized in the entire detector chamber 140. To a certain extent a redistribution of the electrically charged particles 176 and thus a redistribution of the spatial charge within the detector chamber 140 is possible in this way.

The counterelectrode 172, which, as described above, can be regarded electrically or physically also as part of the gate electrode 130, is, as explained above, likewise preferably embodied in a manner insulated from the detector chamber 140. In the exemplary embodiment in accordance with FIG. 1B, alternatively the counterelectrode 172 is arranged in a manner electrically isolated or physically separated from the gate electrode 130. Preferably, however, an electric field can propagate from the counterelectrode 172 to the gate electrode 130 and/or the detector chamber 140, in particular in order to act on the electrically charged particles 176, for example. The counterelectrode 172 can be designed in particular to act on the electric charged particles 176 in such a way that the latter can serve for example for a detection of the analyte 144 that is carried out repeatedly in succession, for example by virtue of the fact that the electrically charged particles 176 can be brought to a starting position again after a detection has been carried out. As illustrated in FIGS. 2A and 2B, the voltage source 174 that can be changed over, with its changeover switch 175, can be connected to said counterelectrode 172. Said voltage source 174 can be connected for example between the counterelectrode 172 and the gate electrode 130 and/or between the counterelectrode 172 and one of the two electrodes 136, 138. However, further configurations are also possible, in principle.

As already explained above, the counterelectrode 172 can be electrically contact-connected, in particular, and a defined potential can preferably be applied to it. In the exemplary embodiment in FIGS. 2A and 2B, for example the voltage source 174 is connected between the counterelectrode 172 and the drain electrode 138, and in FIGS. 1A and 1B, the voltage source 174 is connected for example between the counterelectrode 172 and ground. The voltage source 174 can apply a DC voltage or an AC voltage or a voltage sequence, for example a pulsed voltage sequence, for example to the counterelectrode 172. If, by way of example, the negative pole of the voltage source 174 is connected to the counterelectrode 172, then an electric field E acts on the by way of example negatively charged GM 176, which are driven in the direction of the gate electrode 130 by said electric field. In the exemplary embodiment associated with FIG. 1A, exactly one voltage source 174 is provided for example for both counterelectrodes 172. The same or at least a mutually proportional voltage sequence can thereby be applied in particular to both counterelectrodes 172, whereas the exemplary embodiment associated with FIG. 1B has in particular two separate voltage sources 174 for the counterelectrode 172, whereby different voltage sequences can be applied to the counterelectrode 172 of the electrical sensor 112 and of the compensation sensor 113.

Furthermore, in the detector chamber 140, for example the detector substance 150, once again one or a plurality of receptors 160 are provided, which for example can once again be configured with the properties described with reference to FIGS. 1A and 1B and to which the analyte 144, for example glucose, can bind. The receptors 160 are configured for example in such a way that they are arranged between the electrically charged particles 176 in their position furthest away from the gate electrode 130 and the gate electrode 130. By way of example, once again an affinity binding with the analyte 14 can take place. If many analyte molecules, for example glucose molecules, stay for example at the affine binding sites of the receptors 160, since the analyte concentration, for example the glucose concentration, is high, then the electrically charged particles 176 cannot pass so close to the gate electrode 130, that is to say for example to the semiconductor 132 and/or the organic semiconductor 134, in particular the conductive polymer. Consequently, in this case, which is illustrated in FIG. 2A, the electric field acting on the gate electrode 130 and thus on the semiconductor 132 or the organic semiconductor 134 is lower. This results, for example, in a higher conductivity of the π-electrons in the conductive polymer. If, by contrast, as illustrated in FIG. 2B, few analytes 144, for example few glucose molecules, are present, then many of the binding sites of the receptors 160 are unoccupied and the electrically charged particles 176 can pass on average closer to the gate electrode 130. Accordingly, a higher negative electric field acts on the charge carriers in the semiconductor 132 or organic semiconductor 134, in particular on the conductive polymer. By way of example, depending on the type of semiconductor, the current flow through the semiconductor 132 or organic semiconductor 134 can decrease as a result. In principle, alternatively or additionally, an enhancement principle can also be applied in the case of field effect transistors 114.

As furthermore indicated in FIG. 2B, the receptors 160 can behave neutrally relative to the electrically charged particles 176, that is to say not bind therewith. Alternatively or additionally, however, the receptor 160 can also bind to the electrically charged particles 176, for example reversibly, such that once again an affinity can be provided.

In order that generally the analyte-affinity system can be better adapted to an analyte concentration that has possibly changed in the meantime, and/or in order that variations can be ascertained more rapidly and more precisely in terms of metrology, the positions of the electrically charged particles 176 can be modulated in particular by alternating application of the potential in the system, for example to the gate electrode 130 and/or the counterelectrode 172, for example as a result of repeated changeover, for example periodic changeover, of the voltage source 174 by means of the changeover switch 175.

The effective electric field E is generally a vectorial quantity and dependent on the distance s between the resulting potential and the plane of the gate electrode 130 and/or of the semiconductor 132 or organic semiconductor 134, for example the conductive polymer:

$$E = \frac{U_1}{s_1} + \frac{U_{Spacer}}{s_{Spacer}}.$$

In this case, the designations have the following meanings:
E=electrically effective total field
$s_1$=distance between gate electrode 130 and counterelectrode 172 and/or between counterelectrode 172 and semiconductor 132 or organic semiconductor 134,
$U_1$=voltage between gate electrode 130 and counterelectrode 172 and/or between electrode 136, 138 and counterelectrode 172,
$U_{spacer}$=total voltage of all electrically charged particles 176,
$s_{spacer}$=distance between the electrically charged particles 176 and the gate electrode 130 and/or the semiconductor 132 or organic semiconductor 134, and $$U_{Spacer} = \frac{n \cdot Q \cdot s_{Spacer}}{\varepsilon \cdot A},$$

where:
n=number of electrically charged particles 176,
Q=elementary charge≈$1.6 \cdot 10^{-19}$ As,
$\varepsilon$=the permittivity of free space≈$8.854 \cdot 10^{-12}$ As/Vm, A=effective area of the electrically charged particle 176, $$E = \frac{U_1}{s_1} + \frac{n \cdot Q}{\varepsilon \cdot A},$$

$$n = F \cdot \int C_A \cdot dt_{residence}$$

where
F=proportionality factor,
$c_A$=analyte concentration,
$t_{residence}$=average time for which a particle of the analyte 144, for example an analyte molecule, resides in the system, for example the detector chamber 140 and/or between the electrodes 130, 172.

The residence duration is as a rule in particular dependent on the degree of affinity of the analyte molecules for the receptors 160 used.

The resulting field strength is thus overall:

$$E = \frac{U_1}{s_1} + \frac{F \cdot Q \cdot \int C_A \cdot dt_{residence}}{\varepsilon \cdot A}.$$

The charge carrier mobility in the semiconductor 132, in particular the organic semiconductor 134, is in many cases at least approximately dependent on the field strength:

$$L = k \cdot E,$$

where L has the dimension of a conductance and where k is a specific factor of the semiconductor 132, in particular of the organic semiconductor 134 and particularly preferably of the conductive polymer. The following thus results for the measurement current $I_M$:

$$I_M = L \cdot U_2,$$

This current $I_M$ acts for example via the measuring resistor 180 in FIGS. 2A and/or 2B and/or via one or both of the fixed resistors 124, 126 in FIGS. 1A and 1B, in particular via the fixed resistor 124. The measurement signals $S_1$ and $S_2$ are generated in this way. Since, in principle, the quantities dealt with are in part vectorial quantities, in particular the directions thereof, for example field directions, that is to say the signs thereof, can also be exchanged in principle, that is to say that the arrangement which is elucidated in FIGS. 2A and 2B and which is also applicable to FIGS. 1A and 1B is in principle also effective for electrically charged particles 176 in the form of positive charges.

As described above, the structure illustrated in FIGS. 2A and 2B can be arranged in particular in accordance with FIGS. 1A and 1B, that is to say can be integrated into an operational amplifier 118. If it is assumed that the field effect transistors 114, in particular the organic field effect transistors 116, and/or the geometrical structures are identical, then the additive terms are subtracted, such that the following hold true for example for the analyte signal $S_A$:

$$S_A = \frac{U_2 \cdot k \cdot F \cdot Q \cdot t_{residence}}{\varepsilon \cdot A}(1 - C_A),$$

wherein $c_A$ is the average concentration of the analyte 144 in the time interval.

Since preferably, but not necessarily, no reagent which is consumed during the detection of the analyte 144 is provided in the detector substance 150, in principle the system of the sensor device 110 can be serially adjusted in an in vitro reference, for example in order to generate a signal $S_{ref}$ with respect to an analyte concentration $c_{ref}$ before the sensor device 110 is completely or partly implanted into a body tissue, for example. An adjustment factor A can then result for example as follows:

$$A = \frac{S_A}{S_{Ref}} = \frac{1 - c_A}{1 - c_{ref}}$$

Figure 3:
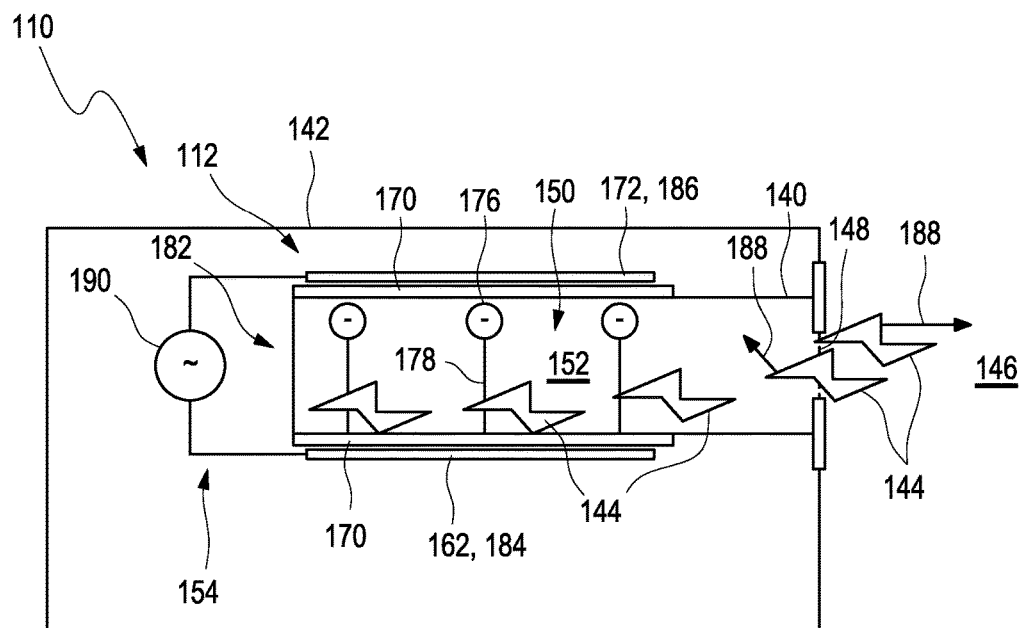
FIGS. 3A and 3B show an exemplary embodiment of a sensor device with a capacitor, with analyte (FIG. 3A) and without analyte (FIG. 3B)
Figure 3:
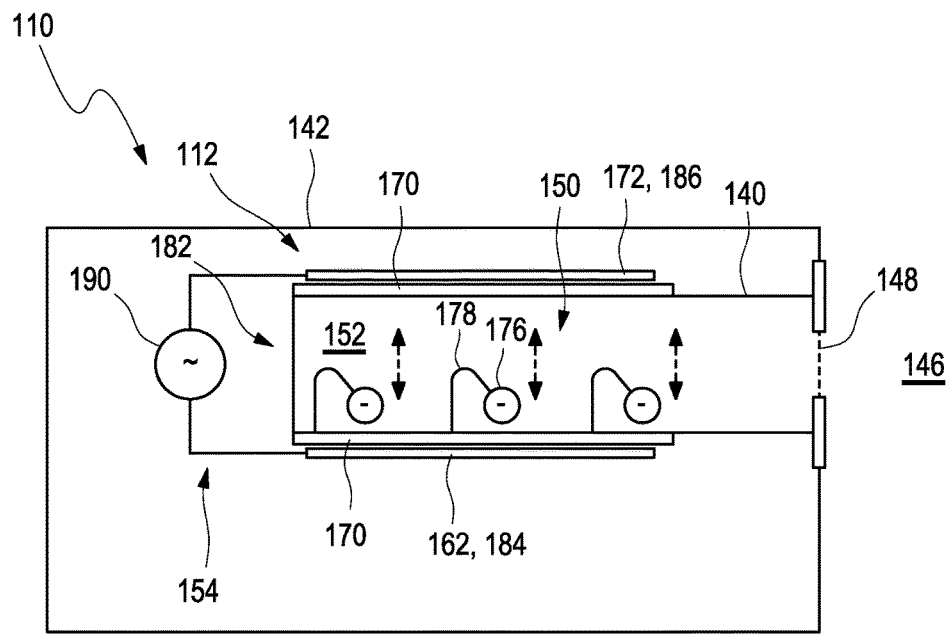

The factor A can be transferred to the sensor device 110, for example the driving unit 154. By way of example, the factor A can be stored and/or processed in the sensor device 110 and/or in a data processing device spatially separated therefrom and/or can be transferred to a control program and/or an evaluation program. FIGS. 3A and 3B illustrate a further exemplary embodiment of a sensor device 110 according to the invention, which can be used for example according to an alternating field principle. In this exemplary embodiment, the sensor device 110 comprises for example an electrical sensor 112 in the form of one or a plurality of capacitances, that is to say at least one capacitor 182. The latter can in principle be constructed similarly to the cell in accordance with FIGS. 2A and 2B and can comprising a first electrode 184, which can be embodied as sensor electrode 162, for example, and a second electrode 186, which can act as counterelectrode 172, for example. Once again a detector chamber 140 and/or part thereof is introduced between these electrodes 184, 186, and with regard to the configuration thereof reference can once again be made by way of example to the above description of FIGS. 2A and 2B. However, other configurations are also possible, in principle. The electrodes 184, 186 can for example once again be configured directly at the detector chamber 140 and/or the medium in the detector chamber 140, but can also preferably once again be configured in a manner insulated therefrom and from one another by one or a plurality of spacers 170, for example insulator layers.

By way of example, once again one or a plurality of detector substances 150 can be accommodated within the detector chamber 140. Once again the detector substance 150 can be configured in particular in such a way that a charge distribution within the detector chamber 140, in particular between the electrodes 184, 186, can be influenced, particularly specifically, by the presence of one or a plurality of analytes 144. The at least one analyte 144, for example glucose, can once again be for example in a diffusion equilibrium with an external environment of the sensor device 110, in particular of the electrical sensor 112, for example a surrounding body tissue, for example with a fluid 146, in particular interstitial fluid 146. This equilibrium is indicated by the reference numeral 188 in FIG. 3A, as also in FIG. 2A. In this way, by way of example, in particular by means of the membrane 148, within the detector chamber 140 it is possible to establish an equilibrium 188 of the analyte concentration with respect to a space outside the electrical sensor 112, in particular in a surrounding body tissue.

In particular, the at least one sensor electrode 162, it also being possible for both electrodes 184, 186 in principle to be configured as sensor electrodes 162, can be configured in such a way that it binds the analyte 144. For this purpose, by way of example, once again one or a plurality of receptors 160 can be provided on the at least one sensor electrode 162, which receptors are not illustrated in FIG. 3A but can optionally likewise be present. The electrically charged particles 176 can for example once again be bound by spacers 178 to the sensor electrode 162 and/or in a different way to the detector chamber 140 or, alternatively or additionally, can also be completely or partly freely mobile, analogously to the configuration in accordance with FIGS. 2A and 2B. Once again, in this or else in some other way, a charge distribution within the detector chamber 140 can be influenced by the presence or absence of the analyte 144, which is once again detectable by means of the electrical sensor 112, for example by means of at least one electrical property of the capacitor 182.

FIGS. 3A and 3B thus show an exemplary embodiment according to which, by way of example, chemical and/or physical processes are converted directly into electrically evaluatable signals. In this case, the analyte-specific electrical sensor 112 is embodied by way of example directly as a capacitor 182. The latter can be provided with the driving unit 154, for example, in order to measure the at least one electrical property which is influenced directly or indirectly by the presence of the analyte 144. By way of example, the capacitor 182 can be used to detune a frequency generator. Alternatively or additionally, the driving unit 154 can, however, also comprise at least one AC voltage generator 190 and/or at least one AC current generator which is connected to the electrodes 184, 186. By way of example, in order to detect the electrical influencing, it is possible to measure a work which has to be expended in such an AC voltage generator 190 and/or frequency generator if the latter is connected to the capacitor 182. The work may be expended in particular for the change of the charge distribution, in particular for a charge movement, for example in association with a movement of at least one of the spacers 178, in the electric field. In order to be able to expend this work, energy can be fed to the system preferably from outside, in particular from outside the electrical sensor 112, for example via the voltage $U_1$.

By way of example, in the arrangement in accordance with FIGS. 3A and 3B, once again as electrically charged particles 176 large molecules can be introduced uniformly and/or in a localized fashion and/or else freely in the detector chamber 140. Once again fluid 146 and/or analyte 144 can enter into the detector chamber 140. The two electrodes 184, 186 can be fitted to the detector chamber 140. The electrodes 184, 186 can be connected to the AC voltage generator 190. If analyte 144 passes into the detector chamber 140, in a manner similar to that in FIGS. 2A and 2B, then the electrically charged particles 176 can be impeded in terms of their mobility depending on the concentration of the analyte 144 and the dielectric forces can increase, encompassing for example in particular an increase in the dielectric factor of at least one portion of the detector chamber 140. The processes in the detector chamber 140 are thus comparable to the above description in FIGS. 2A and 2B. This once again means that the work that has to be applied for example by the AC voltage generator 190 and/or in other components of the system in order to hold a frequency, for example, likewise increases. Without analyte 144, the mobility is higher, for example, and the dielectric forces decrease, encompassing for example in particular a decrease in the dielectric factor of at least one portion of the detector chamber 140. In general, less work then has to be applied in the system. The work applied by the driving unit 154, for example, is therefore a measure of the concentration of the analyte 144 in the detector chamber 140, for example by virtue of said work being proportional to the concentration of the analyte 144. Furthermore, the average residence duration is once again of importance. Consequently, the work expended by the driving unit 154 can therefore be dependent on the analyte concentration in the environment of the electrical sensor 112, for example in the body tissue, in particular a glucose concentration in the interstitium. FIG. 3A illustrates once again, analogously to FIG. 2A, a case in which a high concentration of analyte 144 is present, such that a high degree of work has to be expended, whereas a low analyte concentration is present once again in FIG. 3B, analogously to FIG. 2B, such that a comparatively low degree of dielectric work has to be expended.

The dielectric constant of the capacitor 182 is generally dependent on the mobility of the electrically charged particles 176, which can be configured as particles having a net charge or else as electric dipoles or multipoles. By way of example, a dielectric constant may be dependent on a mobility of electric dipoles. Consequently, if the electrically charged particles 176, if appropriate including the spacers 178, are less mobile, for example owing to the high concentration of the analyte molecules of the analyte 144, then the dielectric constant increases. In the simple parallel-plate design of the capacitor 182 as illustrated by way of example in FIGS. 3A and 3B, for example the energy W stored in the capacitor 182 can be expressed by:

$$W = \frac{\varepsilon \cdot E^2 \cdot A \cdot s}{2},$$

where W is the work or stored energy, where E is the effective field strength, that is to say the root-mean-square value of the alternating field strength, E is a dielectric factor, where A is the area of the arrangement, and where S is the distance between the electrodes 184, 186 of the capacitor 182. The electrical energy W can be measured by the generator AC voltage of the AC voltage generator 190 being detected. By way of example, into the latter has to be increased at relatively high concentration in order to keep the frequency constant. Conversely, however, given constant generator voltage, the frequency of the oscillation of the electrically charged particles 176 can vary depending on the concentration of the analyte 144. Therefore, the concentration of the analyte 144 can be converted directly into a digitally evaluatable signal, for example into oscillations per time interval, and these can be counted, for example. The following results here:

$$\varepsilon = k \cdot c_A,$$

where:

$$C = \frac{\varepsilon \cdot A \cdot}{s} = \frac{k \cdot c_A \cdot A}{s},$$

C=capacitance of the capacitor 182 in farads, and
k=a factor dependent on the overall system.

A direct relationship between the analyte concentration and the electrical measurement variable can be achieved for example if the electrical sensor 112 and/or the capacitor 182 as frequency-influencing capacitance are/is connected into an oscillator, for example into an electrical resonant circuit. The resonant circuit frequency f can then result for example as:

$$f = \frac{1}{2\pi\sqrt{LC}} = \frac{1}{2\pi\sqrt{\frac{kc_A A}{s}}},$$

where L is an inductance of the resonant circuit and $c_A$ is once again the analyte concentration.

As an alternative or in addition to a resonant circuit, however, it is also possible to use other types of oscillation circuits, for example oscillation circuits using field effect transistors 114, such as, for example, Colpitts oscillators or similar oscillators.

Figure 4:
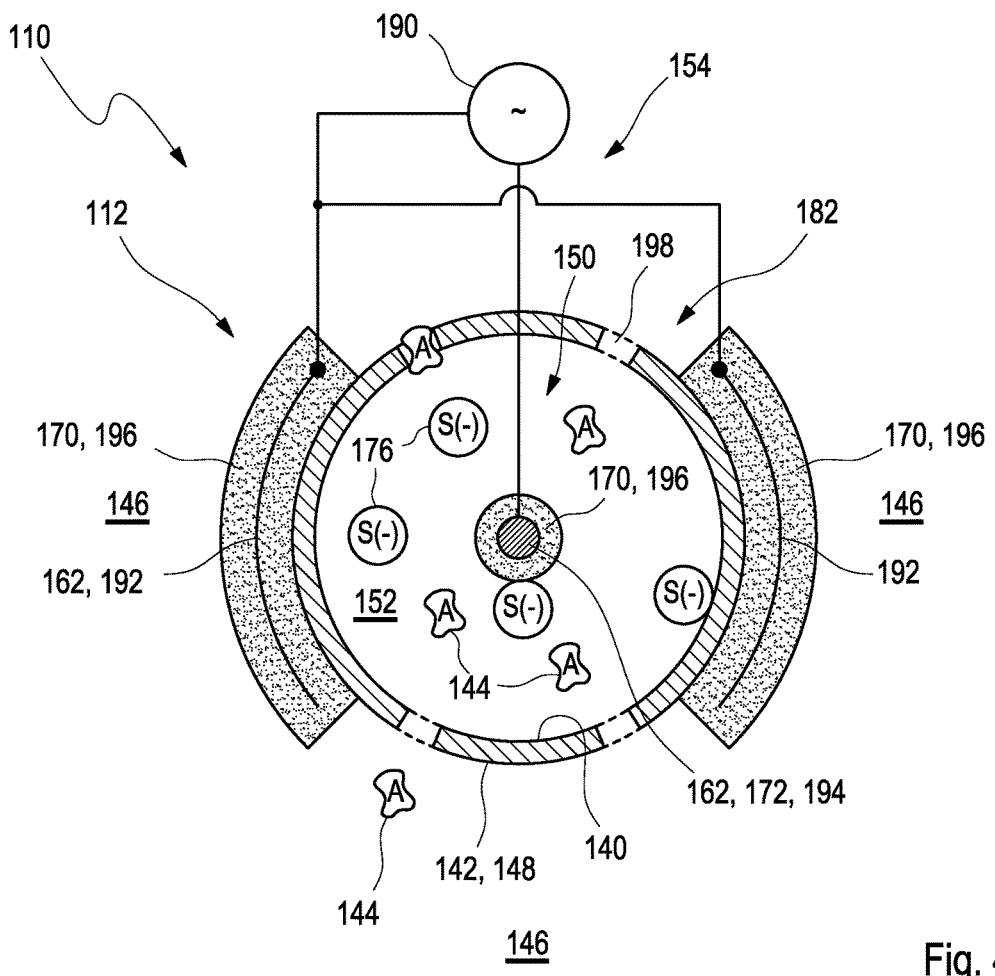
FIG. 4 shows an exemplary embodiment of a sensor device with a cylindrical capacitor.

FIG. 4 illustrates a further exemplary embodiment of a sensor device 110 having an electrical sensor 112, which once again comprises one or a plurality of capacitors 182. A cross section through the electrical sensor 112 is illustrated, in contrast to FIGS. 2A-3B, which show longitudinal sections parallel to an insertion direction of the electrical sensor 112. In this configuration, the capacitor 182 of the electrical sensor 112 once again comprises electrodes 192, 194, in a concentric, for example coaxial, construction. In this case, one of said electrodes 192, which is configured in a bipartitate fashion by way of example in this exemplary embodiment but which can also be configured, in principle, integrally or with more than two parts, is arranged on a lateral surface of a cylindrical housing 142 of a detector chamber 140. By way of example, this bipartite electrode 192 can once again be separated from the detector chamber 140 by one or a plurality of spacers 170, for example by one or a plurality of insulators 196, into which said electrode 192 can be embedded. By way of example, organic and/or inorganic insulators can be involved in this case.

The second electrode 194 can once again be embodied as a counterelectrode 172 and, in this exemplary embodiment, by way of example, is configured as a central electrode, for example as a central wire and/or central pin. This central electrode 194, too, can for example once again be insulated from a fluid medium 152 accommodated in the detector chamber 140 by one or a plurality of spacers 170, for example once again by one or a plurality of insulators 196.

In this exemplary embodiment, one or both of the electrodes 192, 194 can serve as sensor electrode 162, by means of which the at least one electrical property which can be influenced by the presence of the at least one analyte 144 can be detected.

In the exemplary embodiment illustrated, the housing 142 is configured as semipermeable to the analyte 144. This means that the analyte 144 can for example once again form an equilibrium 188 between the surrounding fluid 146 and the fluid medium 152 within the detector chamber 140. By way of example, for this purpose, the housing 142 can be configured completely or partly as a semipermeable membrane 148 which is permeable to the analyte 144 but which can retain for example a detector substance 150 and/or constituents thereof in the interior of the detector chamber 140. Said at least one detector substance 150 can for example once again, analogously to the example in accordance with FIGS. 3A and 3B, comprise at least one type of electrically charged particles 176, for example once again as illustrated in FIG. 4 negatively charged particles, for example negatively charged molecules.

The sensor device 110 in accordance with FIG. 4 can once again contain a driving unit 154, for example a driving unit 154 analogously to the exemplary embodiment in FIGS. 3A and 3B. Once again this driving unit 154 can comprise for example at least one AC voltage generator 190 which can be connected to the bipartitate first electrode 192 by one terminal and to the counterelectrode 172 by another terminal. By way of example, the sensor device 110 in accordance with FIG. 4 can also be part of at least one phase-locked loop (PLL). However, further circuitry arrangements are also possible, in principle.

The sensor chemical system in the interior of the detector chamber 140 can once again be configured in various ways. By way of example, the electrically charged particles 176 can once again bring about a charge distribution in the interior of the detector chamber 140, depending on a concentration of the analyte 144. The electrically charged particles 176 can for example once again be bound to one or a plurality of inner surfaces of the detector chamber 140 by means of spacers 178. Alternatively or additionally, however, the electrically charged particles 176, as illustrated in FIG. 4, can also be freely mobile within the detector chamber 140. Once again alternatively or additionally, the at least one detector substance 150 can also, analogously to FIGS. 3A and 3B and FIGS. 2A and 2B, once again optionally comprise at least one receptor 160, for example at one or both electrodes 192, 194, for example in order, in the presence of analyte 144, to restrict the movement latitude of the charged particles 176. Alternatively or additionally, however, solely the displacement effect as a result of the analyte 144 can also suffice to bring about a restricted mobility of the electrically charged particles 176 and thus an altered dielectric behavior in an alternating field of the capacitor 182.

In vivo sensors, as which the electrical sensor 112 can be used (as an alternative or in addition to use as an in vitro sensor), the analyte 144 preferably not being chemically converted in these sensors, could theoretically work for a very long time without being replaced. Physiological properties in the body, however, have the effect that generally a sensor surface becomes clogged after a certain time, for example by protein deposits, coagulation products or similar effects. Nevertheless, higher long-term stabilities compared with conventional subcutaneous sensor systems arise. Consequently, a possibility for the subcutaneous scope of the electrical sensor 112 or parts thereof by minimally invasive interventions is made possible, and the proposed electrical sensors 112 in accordance with one or more of the exemplary embodiments described and/or other exemplary embodiments according to the present invention is advantageous relative to conventional sensor elements with substance conversion. Such a sensor element could be introduced into a subcutaneous tissue in practice for example as a catheter-type, membrane-enclosed, preferably flexible, structure, for example with the configuration described in FIG. 4. By way of example, the detector chamber 140 can have a diameter of for example approximately 1 mm, in particular of 50 µm to 2 mm. The detector chamber 140 can be configured as a capillary, for example, with one or a plurality of openings 198, which are optionally indicated in FIG. 4 and which can be given small dimensions for example in such a way that only the analyte 144, but not the detector substance 150, for example the electrically charged particles 176, can penetrate through them. By way of example, as an alternative or in addition to openings 198, porous wall materials can be used for the housing 142. Once again alternatively or additionally, the openings 198 can also be enclosed and/or filled completely or partly by a membrane 148, for example in accordance with the properties described above, in order to ensure the semipermeable properties described. By way of example, the structure enclosed by a membrane in this way can be introduced into a subcutaneous tissue, in such a way that the electrically charged particles 176 mentioned are enclosed in the detector chamber 140 and, if appropriate apart from the fluid 146, for example interstitial fluid, as far as possible only the analyte 144, for example glucose, can be exchanged through the membrane surface and/or the openings 198. The detector substance 150, in particular the electrically charged particles 176, can now be enclosed in the detector chamber 140 and need no longer necessarily be fixed to a surface by means of spacers 178, but rather can preferably move freely in the detector chamber 140. This considerably reduces the requirements made of the structure and application of the electrically charged particles 176. The spatial structure of the capacitor 182 can be realized for example by a rotationally symmetrical arrangement in accordance with FIG. 4. However, further geometric arrangements are also possible, in principle. By way of example, FIG. 4 illustrates a concentric construction with the rotationally symmetrical central electrode 194, which construction can be realized for example in the form of a hollow catheter. The parts of the first electrode 192 which are insulated in the insulators 196 bear on the outer walls, which parts can be compared as simple electrodes or, analogously to the construction in accordance with FIGS. 3A and 3B, or as constituents of one or a plurality of field effect transistors 114, analogously to the construction in accordance with FIGS. 2A and 2B. Other geometrical constructions are also possible, however, for example with a plurality of counterelectrodes 172, with differently shaped outer electrodes 192 or with non-rotationally symmetrical constructions. The outer electrodes 192 are preferably configured in such a way that situated between them are free areas of the housing 142 through which the analyte 144 can pass out of and into the detector chamber 140, for example by permeation through a membrane 148.

Figure 5:
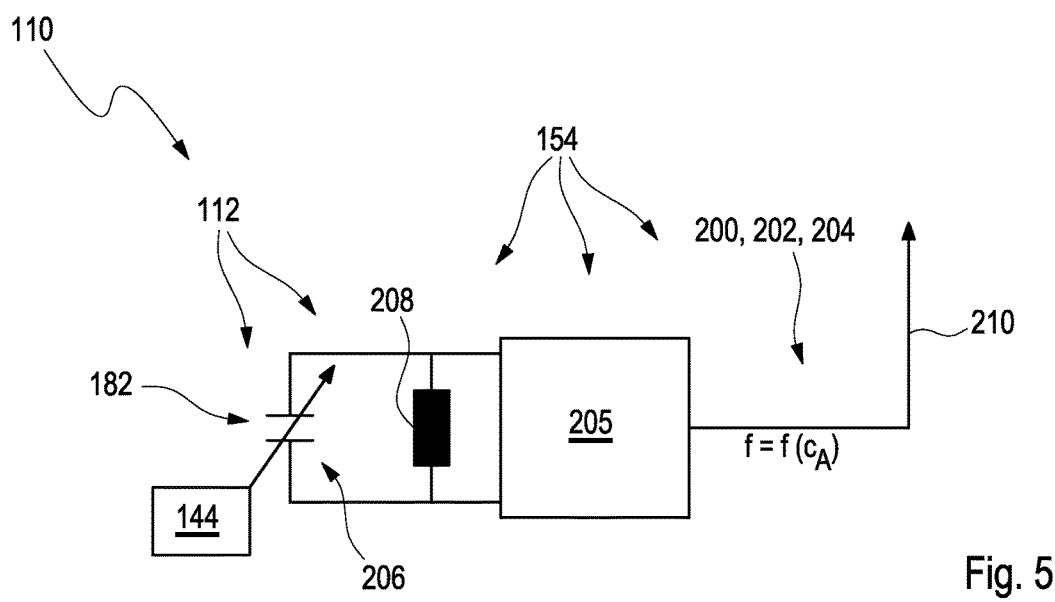
FIG. 5 shows a block diagram of a possible configuration of a sensor device.

As described above, capacitive systems, having at least one capacitor 182, are particularly well suited to detection of at least one electrical property influenced by the analyte 144. In particular, as explained above, at least one frequency of at least one oscillator can be influenced by a capacitance and/or by the electrical properties of the capacitor 182. This influenced frequency and/or a signal derived therefrom can be output by the sensor device 110 for example via at least one interface, which is designated by the reference numeral 200 in an exemplary embodiment in accordance with FIG. 5, for example via at least one wireless interface 202, in particular a radio interface 204. FIG. 5 shows a schematic construction of a sensor device 110 by means of which this principle can be realized. In this case, by way of example, a driving unit 154 of the sensor device 110, the electrical sensor 112 of which can be configured for example in accordance with the exemplary embodiments in FIG. 3A, 3B or 4, can contain at least one oscillator 205 which excites a resonant circuit 206. Besides the at least one capacitor 182, said resonant circuit 206 can for example furthermore comprise at least one coil 208 and/or some other type of inductive element. By means of the resonant circuit 206, the oscillator 205 is set to the resonant frequency of the resonant circuit 206 depending on the analyte 144, which is indicated by an influencing of the capacitance of the capacitor 182 by the analyte 144 in FIG. 5. This frequency f is therefore a function of the analyte concentration $c_A$. The frequency can be forwarded directly or indirectly, for example after conversion by frequency modulation and/or amplitude modulation and/or phase modulation into a further signal via the interface 200, for example via at least one antenna 210. By way of example, this signal can be received by a reader, which is designated by the reference numeral 212 in an exemplary block diagram in accordance with FIG. 6. This can involve for example a reader 212 with a radio receiver and/or an RFID reader. Further configurations are also possible. By way of example, in the configuration in accordance with FIG. 5, in the oscillator 205 of the sensor device 110, a radio carrier frequency can be directly modulated by the properties of the capacitor 182.

Figure 6:
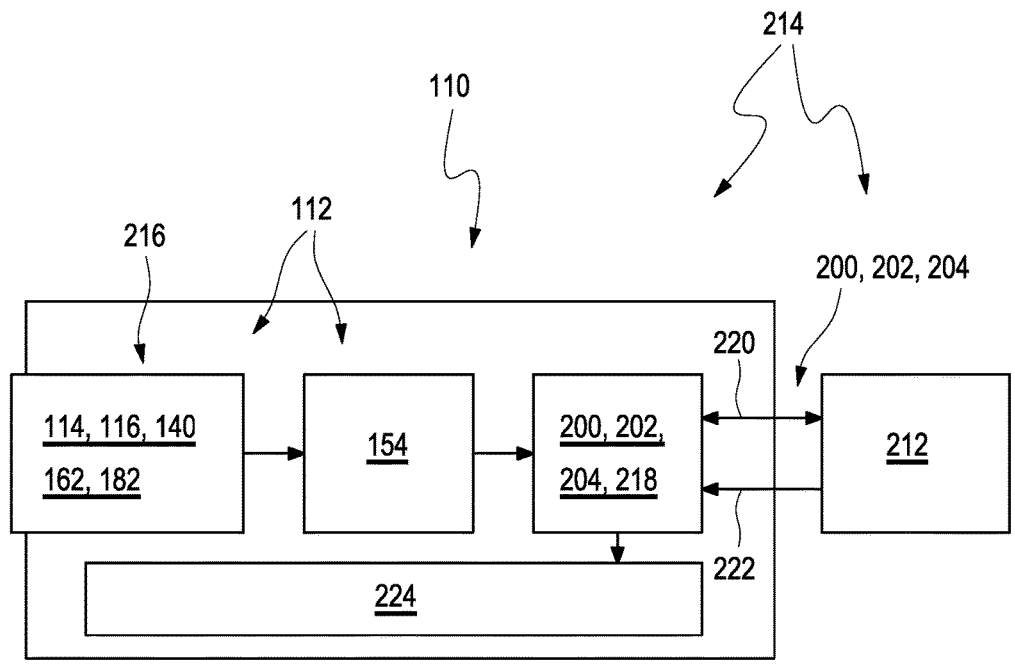
FIG. 6 shows a block diagram of one exemplary embodiment of a sensor system.

FIG. 6 describes an exemplary embodiment of a sensor system 214, which can comprise at least one reader 212 besides at least one sensor device 110 having at least one electrical sensor 112, for example in accordance with one or more of the configurations described above. The electrical sensor 112 can be configured for example in any desired manner according to the present invention and can for example once again comprise one or a plurality of field effect transistors 114, in particular organic field effect transistors 116, and/or one or a plurality of capacitors 182 and/or one or a plurality of sensor electrodes 162, as indicated in FIG. 6. The electrical sensor 112 can comprise in particular an implant 216 and/or a part which can be inserted into a body tissue. Furthermore, the electrical sensor 112 and/or the sensor device 110 can once again comprise at least one driving unit 154 for example a driving unit 154 with signal processing, and/or a driving unit 154 in accordance with one or more of the configurations described above. Furthermore, said driving unit 154 can in particular once again be connected to one or a plurality of interfaces 200 or be partly identical to at least one interface 200 of this type. In the context of the configuration shown in FIG. 6, it is particularly preferred if this at least one interface 200 comprises at least one transponder 218. However, other configurations are also possible, in principle. Via said at least one interface 200, a data exchange 220 with the reader 212 is possible in a unidirectional and also bidirectional manner, for example a capacitive and/or inductive and/or electromagnetic data exchange 220. Furthermore, however, energy can also optionally be fed into the sensor device 110 by the reader 212, this being designated by the reference numeral 222 in FIG. 6. This energy feeding 222 can take place for example analogously to conventional transponders 218, for example RFID transponders, in which electromagnetic energy is fed in by the reader 212 for example capacitively and/or inductively and/or via at least one resonant circuit 206. Alternatively or additionally, the sensor device 110 can also comprise one or a plurality of energy supplies 224, for example an energy supply 224 via an interface 200 and/or an energy supply 224 via at least one internal energy store, for example at least one battery and/or at least one rechargeable battery, and/or at least one energy supply 224 by means of energy being drawn from an environment, for example so-called energy harvesting. If, as described as an option in FIG. 6, energy is fed wirelessly from outside from the reader 212, for example according to a transponder principle, then this can additionally promote a long-term insertion or long-term implantation, since, by way of example, biological rejection effects of supply cables can be avoided and/or since the entire sensor device 110 and/or parts thereof can be configured with a comparatively small volume. Energy can be provided, as described above, for example by means of induction from outside according to the RFID principle.

In the exemplary embodiments in accordance with FIGS. 3A, 3B and 4 or else in other exemplary embodiments of the present invention in which the sensor device 110 has at least one electrical sensor 112 in the form of at least one capacitor 182, it is likewise possible once again optionally to provide one or a plurality of compensation sensors 113, the electrical properties of which are not influenced or are only insignificantly influenced by the analyte concentration. By way of example, in each case one or a plurality of compensation capacitors can be provided, which is not illustrated in the Figs. Said compensation capacitors can for example in turn have two or more electrodes, for example in a configuration analogous to the actual electrical sensor 112, but non-specific with regard to the analyte concentration. By way of example, the at least one optional compensation capacitor can have at least one compensation capacitor electrode and at least one counterelectrode.

Figure 7:
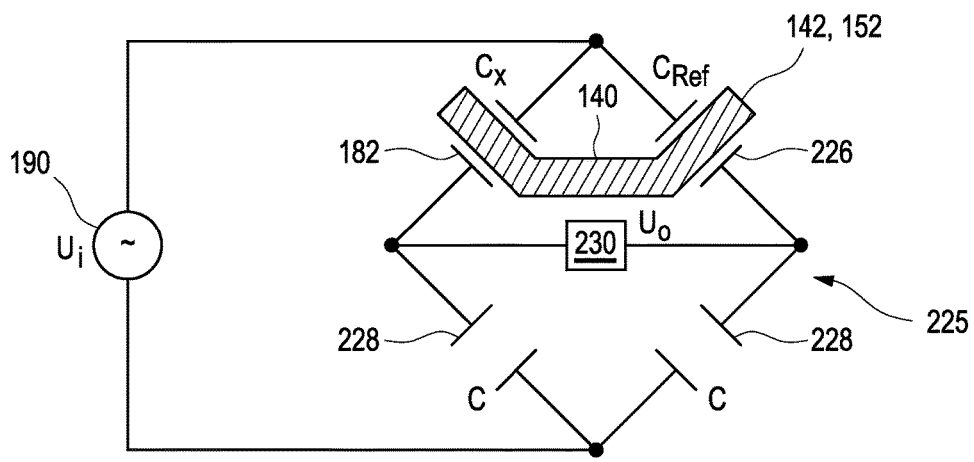
FIG. 7 shows an exemplary embodiment of a sensor device within a measuring bridge.

Furthermore, in the context of the present invention, generally the electrical sensor 112 and/or the compensation sensor 113 can be incorporated into an electrical bridge circuit 225 and/or a compensation circuit. This can be done either in the case of the above-described configurations using one or a plurality of field effect transistors 114 or else preferably in the case of the configurations with one or a plurality of capacitors 182. This is shown by way of example in FIG. 7 on the basis of an exemplary embodiment with capacitors 182. In particular, the at least one capacitor 182 can be part of the bridge circuit 225, in particular a bridge, as in the exemplary embodiment in accordance with FIG. 7, for example. The bridge circuit 225 can comprise in particular at least one capacitor 182, for example configured as electrical sensor 112, and/or at least one compensation capacitor 226, for example configured as compensation sensor 113, and/or optionally at least one, preferably two, bridge capacitors 228 and/or at least one measuring device 230 and/or at least one driving unit 154 and/or at least one detector chamber 140. In principle, this exemplary embodiment can alternatively or additionally also comprise other components, for example as described in the other exemplary embodiments, for example at least one field effect transistor 114.

The electrical sensor 112 and the compensation sensor 113 can be configured for example as described in the exemplary embodiments in accordance with FIGS. 3A and 3B or 4. The bridge capacitors 228 can preferably be configured like capacitors 182. In principle, the bridge circuit 225 can alternatively or additionally also comprise ohmic resistances and/or inductive reactances, for example at least one coil 208.

The fluid medium 152 can at least partly flow around the electrical sensor 112, in particular the capacitor 182 and/or the compensation sensor 113, in particular the compensation capacitor 226. The detector chamber 140 can likewise be configured in a manner similar to the previous exemplary embodiments; in particular, the detector chamber 140 can be arranged at least partly within the electrical sensor 112, in particular the capacitor 182, and/or the compensation sensor 113, in particular the compensation capacitor 226, in particular at least partly in each case between the sensor electrode 162, for example configured as gate electrode 130, preferably as capacitor electrode, and the counterelectrode 172, for example likewise configured as capacitor electrode. The basic construction of the bridge circuit 225 may be known in particular to the person skilled in the art. In the exemplary embodiment in accordance with FIG. 7, by way of example, a series circuit comprising the electrical sensor 112 and one of the two bridge capacitors 228 is connected in parallel with a series circuit comprising the compensation sensor 113 and the other of the two bridge capacitors 228. An AC voltage, in particular an input voltage $U_i$, can be applied to both series circuits in particular by means of an AC voltage generator 190. A bridge diagonal, in particular electrically connecting the two series circuits centrally, can comprise in particular a measuring device 230, preferably in order to detect an electrical voltage, preferably an AC electrical voltage, in particular an output voltage $U_0$. The measuring device 230 can comprise in particular at least one voltage measuring device, preferably at least one AC voltage device, and/or at least one current measuring device, preferably at least one AC current measuring device. A ratio of output voltage $U_0$ and input voltage $U_i$ can be expressed for example by:

$$\frac{U_o}{U_i} = \frac{C_x - C_{ref}}{C},$$

where $C_x$ may represent a capacitance of the electrical sensor 112, in particular of the capacitor 182, $C_{ref}$ may represent a capacitance of the compensation capacitor 226 and/or of the compensation sensor 113, and C may represent a capacitance of at least one, preferably two, bridge capacitors 228. The bridge circuit 225 can therefore be used in particular to determine the capacitance $C_x$ of the electrical sensor 112, which can be determined in particular by a dielectric constant, for example, and the at least one analyte 144 can preferably be detected in this case.

Exemplary Embodiments Regarding the Configuration of the Detector Substance 150:

With regard to the configuration of the detector substance 150, in particular with regard to the electrically charged particles 176 and/or the spacers 178 and/or the receptors 160, there are various possibilities which, in principle, are applicable to all the exemplary embodiments of the present invention. In this case, basically it is possible to distinguish between two principles, which can also be combined with one another, namely the principle of generating affinity without analyte conversion and the principle of generating affinity with analyte conversion.

1. Exemplary Embodiments of Electrically Charged Particles 176:

In the various exemplary embodiments, free electrically charged particles 176 and also optionally electrically charged particles 176 restricted in terms of the mobility by means of at least one spacer 178 can be used as electrically charged particles 176.

By way of example, it is possible to use one or a plurality of types of molecules having charged ionic groups, which can optionally be spacer-bound or which, alternatively or additionally, can be fixed spatially in terms of their functional range and/or movement range by means of a suitable compartmentalization in the detector chamber 140.

The electrically charged particles 176 should generally have the following properties:

a) a molecule size significantly more voluminous than the spacers 178, generally of the order of magnitude of the analyte 144, but preferably no polymers.

b) A defined, uniform structure, ideally spherical (globular, but preferably without chemical or steric affinity for the surface).

c) Buffer properties having the effect that a constant charge and an unambiguous uniform charge, for example always negative, are provided in the region of the prevailing ambient conditions. More critical would be electrically charged particles 176 which would have a varying charge on account of a physiological pH change and are generally ruled out for lack of an only analyte-dependent equilibrium setting between the medium and the surface.

d) For increasing the field strengths a preferably relatively high charge, for example by means of more than one, preferably more than two, anionic groups.
e) Straightforward synthetic accessibility, in particular for the preferred possibility of linking via at least one spacer 178.

Embodiments of electrically charged particles 176 include, for example, polycarboxylic acids of benzene, that is to say benzenecarboxylic acids. The latter are generally also very good buffers since they bring about a smoothing of the pKa values of the individual acid groups as a result of interaction via hydroxylic H bonds between adjacent dissociated and undissociated carboxyl groups. This means that the pKa values of the individual stages are generally close together given deliberate positioning of the carboxyl groups, with the result that pH changes are buffered outstandingly without a basic charge reversal, that is to say from negative to neutral or positive, arising in principle. Alternatively or additionally, pKa jumps are present on account of the positioning. In other words, there is a variable diversity in this substance class.

As examples which can also be combined arbitrarily in pairs or in groups among one another or with other examples, for the electrically charged particles 176 in particular the prototype of the polybasic benzenecarboxylic acids is appropriate, to be precise selected from the group consisting of benzenedicarboxylic acid (H2), for example phthalic acid, benzenetricarboxylic acid (H3) of different types, for example trimesic acid or trimellitic acid, benzenetetracarboxylic acid (H4), for example pyromellitic acid, benzenepentacarboxylic acid (H5) and benzenehexacarboxylic acid (H6), (mellitic acid); wherein in the latter a linking to the spacer 178 would be possible only via one of the six carboxyl groups, and for example molecules derived from the substances mentioned, for example dimers and/or trimers and/or oligomers and/or alternatively the complexes thereof with metal cations and/or with protenated organic bases, for example alkylamines and/or heterocyclic compounds comprising in each case a plurality of basic amino groups and/or nitrogen atoms. Mellitic acid is appropriate, as mentioned, if a spacer 178 bound to its carboxyl group is preferred, in particular since, on account of the arrangement of the carboxyl groups of mellitic acid, mellitic acid would be fixed with a close fit on the surface and, consequently, would have for example hardly any or no freedom of movement.

2. Exemplary Embodiments of Spacers 178:

In the case where the electrically charged particles 176 or parts thereof are intended to be linked to at least one surface via at least one spacer 178, for example one or a plurality of the above-described types of ionically present molecules and/or other types of electrically charged particles 176 can be bound to moveable spacers 178, and these spacers 178 can then in turn be anchored by grafting for example on a polymeric surface and/or some other type of organic or inorganic surface.

Examples of movable spacers 178, which can also be combined, are in particular aliphatic chains (alkyl chains), polyether chains, polyimino chains or combinations of the stated and/or other types of spacer 178. In this case, a charge neutrality of the spacers 178 should be ensured. An occupation density and/or a hydrophilicity of the spacer chains can influence the binding of the analyte 144, for example glucose, in the graft region. In specific applications, non-polar spacer chains can also be advantageous, for example for the canalization of an analyte approach, in particular a glucose approach to one or a plurality of receptors 160. On the other hand, in specific cases polar portions in the spacer 178 can lead the analyte 144, for example glucose, more easily to the at least one receptor 160.

3. Exemplary Embodiments of Receptors 160:

There are a number of possibilities for providing the at least one optional receptor 160 in the detector substance 150. In particular, it is possible to generate an analyte-specific affinity to at least one surface within the detector chamber 140, for example a surface of the at least one sensor electrode 162, such that with regard to the receptors 160, without restricting further possible configurations, hereinafter reference is generally made to an affinity. Said receptors 160 make it possible to ensure for example the variation of the charge distribution and/or the variation of other electrical properties, for example the variation of dielectric properties within the detector chamber 140 and/or the variation of electric fields. A detection can take place for example by means of polar groups and dielectric changes.

As described above, the at least one sensor electrode 162 can comprise at least one conductive layer, but can also, alternatively or additionally, simply be or comprise a surface of a component, in particular a surface of a field effect transistor 114, preferably an organic field effect transistor 116, for example a surface of a semiconductor 132, in particular of an organic semiconductor 134. By way of example, a polymer surface can be involved in this case. Alternatively or additionally, between this at least one surface and the detector chamber 140, in particular the medium within the detector chamber 140, at least one spacer 170 can be introduced, as described above, such that a surface for example of the spacer 170 and/or an inner surface of a housing 142 of the detector chamber 140 in the region of the gate electrode 130 or sensor electrode 162 can also be regarded as a relevant surface.

By way of example, an initial polymer surface of the electrical sensor 112 (PSS) can be provided. By way of example, an electrically conducting polymer having a chemically modified sensor surface can be provided, to which surface the analyte 144 can dock via an affinity, reversible bond. This analyte-identifying surface of the sensor electrode 162 and/or generally a surface which has the at least one receptor 160, and/or the receptor 160 itself, are designated hereinafter as sensor surface chemical system (SSCS). The SSCS thus comprises the detector substance 150 or part thereof, in particular the optional receptor 160 or parts thereof, in particular the analyte-specific detection structures and/or parts thereof. The analyte detections explained below are generally based on the variable and temporally resolved approach of charged chemical groups of the SSCS to the polymer surface of the sensor (PSS) and/or to some other surface, whereby the electrical or dielectric properties of the medium in the detector chamber 140 can be influenced.

Since, with respect to the charged groups and, if appropriate, groups bound to an organic material, in particular a polymer, in particular the electric charged particles 176, there are also generally counterions, for example more readily mobile counterions, one prerequisite generally consists in the fact that in the event of charge movements between these two ion types relative to the electrical sensor 112, for example by means of an alternating field being applied, there is a potential gradient, for example dielectric fluctuations arise and the latter can be registered.

A: Generating Affinity without Analyte Conversion

In order to bind the analyte 144 specifically and reversibly, for example by means of suitable receptors 160, generally there is a need for affinity binding sites, for example the binding sites of an analyte-specific enzyme. Preferably, no conversion whatsoever of the analyte 144 takes place despite a detection. The at least one receptor 160 can therefore contain at least one enzyme, for example.

Without an analyte conversion, the conventional detection chain, which usually begins with a chemical conversion, is shortened as much as possible. The preferred exclusion of an enzymatic conversion as an option in the context present invention makes it possible, in principle, to use only the region of the affinity binding sites of an enzyme as binding partner and to disregard the full functionality of the enzyme. This can make the detection capability of the affinity system, for example of the receptor 160, more robust in relation to an inactivation, for example in relation to a denaturation, and reduce a pH dependence, which traditionally concomitantly determines the conversion rate, or even make it insignificant in a sufficiently stable environment, which, if appropriate, is also facilitated by the presence of charged spacer groups.

The original property of an enzyme in traditional sensors is in this case preferably reduced to an affinity substance-specific binding without chemical and/or enzymatic conversion. For the case of detecting glucose as an example of an analyte 144, a consequent step in this direction is the introduction of lectins as receptor 160, which by definition specifically bind sugars. It is therefore particularly preferred if the at least one receptor 160 comprises at least one lectin, for example selected from the group of glucose-binding lectins, in particular those lectins which can be used for glucose detection. One known example is Concanavalin A, also called Con A, which is obtained for example from the sword bean or the jack bean, and/or *Lens culinaris* agglutinin, obtained from the lentil, for example, and/or Pealectin-I (PSA), obtained for example from the pea (*pisum sativum*). The use of Con A as glucose receptor is known in principle from the literature, for example from U. Beyer et al.: Recording of subcutaneous glucose dynamics by a viscometric affinity sensor, Diabetologia (2001) 44:416-423. In this or else in other exemplary embodiments, the detector substance 150 can for example also comprise at least one competitor, for example a competitor which competes with the analyte 144 to be detected for binding to the receptor 160. For the case of Con A as receptor 160 and for example glucose as analyte 144, it is known for example to use glucose-labeled macromolecular dextran (Dex-Gluc4), which competes with free glucose for binding to Con A. Since Dex-Gluc4 and Con A can bind polyvalently, a polymeric adduct of high viscosity rapidly arises in general in an aqueous or physiological medium. As glucose is added, the (generally in each case four) polyvalent linkages of dextran-Gluc and Con A are broken up and replaced by monomeric Con A-(4)-glucose units, as a result of which the viscosity decreases. This mechanism can be used in various configurations in the sensor according to the invention, for example for varying a mobility and/or for influencing a charge distribution and/or for influencing dielectric properties of the medium within the detector chamber 140, for example by occupying one or a plurality of the electrodes, in particular the sensor electrode 162, for example with the aim that charged head groups of the spacers 178 described can approach a surface more or less successfully. The possibility of approach can be for example reciprocally a function of the portions of dextran (Dex-Gluc4)-Con A and thus directly a function of the concentration of free glucose, for example if the mobility of corresponding counterions is configured differently.

A generally risky, continuous supply of the electrical sensor 112, in particular the detector chamber 140, with lectin (for example Con A) is generally not necessary for this. Instead, generally a single, small occupation suffices, for example of the sensor electrode 162 and/or of some other inner surface of the detector chamber 140. In particular the problem of quantitatively dependent toxicity can be ruled out as a result. Ideally, the receptor 160 can be immobilized in the detector chamber 140, for example at the sensor electrode and/or some other electrode and/or at some other inner surface of the detector chamber 140, for example an interior of the housing 142 and/or in some other way within the detector chamber 140, for example in one or a plurality of elements additionally accommodated in the detector chamber 140.

Dextran as further agent, in particular as competitor, is generally non-toxic, for example as a charged reporter molecule which can optionally also for example, but not necessarily, be coupled to a spacer 178. Preferably, here non-toxic substances should likewise be chosen which, as required boundary conditions, generally should have a constant charge and not cross a membrane.

B: Generating Affinity with Analyte Conversion

In order to detect the analyte 144 via its conversion, which is possible as an option besides a conversion-free detection, this generally requires an analyte-specific reagent, for example an analyte-specific enzyme. In general, as main product the converted analyte 144 and one or a plurality of secondary products initially arise. In the case of the traditional detections of an enzymatically converted analyte 144, the secondary products are then often converted further by means of a specific test chemical system and only then are they detected. By way of example, the enzymatic oxidation of glucose involves detecting, rather than the oxidized gluconolacton, the byproduct $H_2O_2$, in particular the reduced oxygen situated therein, via one or a plurality of further subsequent reactions, for example via colorant formation and/or electrochemically. In the case of a measurement principle in the context of the present invention with conversion of the analyte 144, it is now possible in principle to detect said analyte optionally solely by means of the presence and decomposition of the secondary product, but preferably not by means of the further conversion thereof. In this case, too, the traditional detection chain is therefore preferably shortened in the context of the present invention. The following possibilities can be mentioned for such a shortened detection of the analyte 144:

B1: Detection Via a pH-Dependent Volume and Charge Change on the Basis of the Example of Glucose:

By way of example, the primary conversion product $H_2O_2$ decomposes into $H_2O$ and $H^+$ and thus leads to a decrease in the pH value within the detector chamber 140, which can in turn be detected by means of the following mechanism: as sensor surface chemical system SSCS it is possible to use a polyanionic polymer, for example a polyacrylic acid derivative, wherein weakly acidic groups can be present anionically in the swollen state. The polymer can be configured in swollen fashion since it can be hydrophilic and since the charged groups can mutually repel one another. If an analyte-specific reaction in which protons arise then commences, the anionic groups become charge-neutral as a result of protonation. The charge-governed swelling of the polymer thus subsides, which in turn affects the electrical properties of the electrical sensor 112, for example the dielectric properties of the capacitor 182. Alternatively, for example a longitudinal stretching of a polyanion, in particular on account of repulsion of negative charges in the polyanion, can experience for example a structure change in the form of an entanglement, in particular if for example the pH value decreases and/or the stretched polyanion is discharged by protonation.

B2: Definition Via the Charge of Ionic Groups and Dipole Moments:

If a swelling of the detector substance 150 and/or of parts thereof takes place in the presence and/or absence of the analyte 144, such that a swelling state of the detector substance 150 and/or of parts thereof changes, then this swelling can be registered by the electrical sensor 112 for example by means of additional charges at the sensor electrode 162 and/or the distances thereof from the sensor electrode 162, for example by means of additional charges of the polymer and/or the distances thereof from the polymer surface of the sensor (PSS). In this regard, by way of example, additional charges of stable anions of relatively high acid strength, for example sulfonates and/or heparin-like polymers, can be registered as a function of their distance from the PSS in the detector chamber 140. This would mean that in a swellable, for example hydrophilic, polymer, functional groups could be present which become charge-neutral during protonation and reduce the swelling. Furthermore, this would mean that some other groups could still remain charged if an enzyme supplies inter alia protons, for example, as a result of the conversion of the analyte 144. Furthermore, this could mean that the mobility of charged groups can be tracked by the electrical sensor 112, on the basis of change in electrical properties of the electrical sensor 112. Owing to the different water content on account of the swelling, the dipole moment of the swellable detector substance 150, for example of the swellable polymer layer, at the sensor electrode 162 could then also or preferably represent a measure of the glucose concentration or generally the analyte concentration.

B3: Adjustment:

Since, in the electrical sensor 112, for example, two regions can be present which can differ for example only in the statement analyte binding: yes/no or enzyme activity: present/not present, analyte-nonspecific variations such as, for example, an increase in pH value in the detector chamber 140 would be identifiable for example after a short time, that is to say that the fact of an analyte-governed pH increase would generally be detectable in relation to a nonspecific change.

B4: Regeneration Phases:

An analyte-governed pH decrease would lead for example as a result of diffusion to a pH balancing
a) between different regions of the detector chamber 140, for example between two compartments of the detector chamber 140, and thereby level the differential signal, and/or
b) between an interior of the detector chamber 140 and a membrane-separated body fluid.

Since the diffusion of analyte 144, in particular glucose, and also a pH balancing generally proceed continuously, the design of the sensor device 110, in particular of the detector chamber 140, should ensure that a specific analyte concentration, for example a specific glucose content is faced with a stable unambiguous sensor signal that correlates with the analyte concentration. By way of example, a pH balancing could proceed more rapidly into a periphery than between different sensor components of the sensor device 110.

B5: Detection by Means of Detecting a Swelling Pressure:

A further possibility for the configuration of the detector substance 150 consists in turn in ensuring an analyte-governed swelling of a least one component of the detector substance 150. By way of example, a pH-governed swelling can in turn be detected directly or indirectly. By way of example, a detector chamber 140 having two or more compartments can be used. By way of example, a nonspecific swelling, since it takes place from an external side, would then be of the same size. The enzyme-governed swelling proceeding in a compartment, for example, would be superimposed on that. The swelling itself could be registered by means of a pressure sensor system, for example, provided that a suitable membrane 148 could prevent pressure equalization toward the outside. A pressure could act on the capacitor 182 for example in the form of a change in distance and thus a change in capacitance, for example by means of an elastomer. Changes in distance and thus changes in capacitance could be obtained in this way and in turn be usable in one or more of the methods and sensor devices 110 described above.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

| List of Reference Signs | |
|---|---|
| 110 | Sensor device |
| 112 | Electrical sensor |
| 113 | Compensation sensor |
| 114 | Field effect transistor |
| 116 | Organic field effect transistor |
| 118 | Operational amplifier |
| 120 | Resistance branch |
| 122 | Resistance branch |
| 124 | Fixed resistor |
| 126 | Fixed resistor |
| 128 | Subtracting stage |
| 130 | Gate electrode |
| 132 | Semiconductor |
| 134 | Organic semiconductor |
| 136 | Source electrode |
| 138 | Drain electrode |
| 140 | Detector chamber |
| 142 | Housing |
| 144 | Analyte |
| 146 | Fluid |
| 148 | Membrane |
| 150 | Detector substance |
| 152 | Fluid medium |
| 154 | Driving unit |
| 156 | Supply voltage |
| 158 | Current source |
| 160 | Receptor |
| 162 | Sensor electrode |
| 163 | Compensation sensor electrode |
| 164 | Nonspecific molecules |
| 166 | Voltage source |
| 168 | Substrate |
| 170 | Spacer |
| 172 | Counterelectrode |
| 174 | Voltage source |
| 175 | Changeover switch |
| 176 | Electrically charged particles |
| 178 | Spacer |
| 180 | Measuring resistor |
| 182 | Capacitor |
| 184 | First electrode |
| 186 | Second electrode |
| 188 | Equilibrium |
| 190 | AC voltage generator |
| 192 | Electrode |

-continued

List of Reference Signs

| | |
|---|---|
| 194 | Electrode |
| 196 | Insulator |
| 198 | Opening |
| 200 | Interface |
| 202 | Wireless interface |
| 204 | Radio interface |
| 205 | Oscillator |
| 206 | Resonant circuit |
| 208 | Coil |
| 210 | Antenna |
| 212 | Reader |
| 214 | Sensor system |
| 216 | Implant |
| 218 | Transponder |
| 220 | Data exchange |
| 222 | Energy feeding |
| 224 | Energy supply |
| 225 | Bridge circuit |
| 226 | Compensation capacitor |
| 228 | Bridge capacitor |
| 230 | Measuring device |

The invention claimed is:

1. A sensor device for detecting at least one analyte in a fluid, comprising at least one closed detector chamber and at least one electrical sensor comprising at least one sensor electrode, wherein the detector chamber can be connected to the fluid in such a way that the analyte can penetrate into the detector chamber, wherein the detector chamber comprises at least one detector substance, wherein the detector substance is configured to influence at least one electrical property of the electrical sensor, depending on a concentration of the analyte in the detector chamber, wherein the detector chamber accommodates at least one receptor, the receptor being formed by a substance distinct from the detector substance and wherein the receptor is configured to bind the analyte reversibly; and wherein the detector chamber comprises at least one membrane, wherein the membrane is configured to enable the analyte to penetrate into the detector chamber reversibly and wherein the membrane is configured to retain the at least one detector substance in the detector chamber.

2. The sensor device of claim 1, wherein the detector substance comprises electrically charged particles.

3. The sensor device of claim 2, wherein the detector chamber and the detector substance are configured in such a way that an average distance between the electrically charged particles and the sensor electrode and/or a charge distribution within the detector chamber are dependent on a concentration of the analyte in the detector chamber.

4. The sensor device of claim 2, wherein the detector substance furthermore comprises at least one spacer, wherein the spacer is designed to bind the electrically charged particles to the sensor electrode and/or a surface of the detector chamber at the sensor electrode, wherein the spacer is designed to assume at least two positions in which the electrically charged particles are at different distances from the sensor electrode.

5. The sensor device of claim 1, wherein the detector substance is configured in such a way that dielectric properties of the detector substance are dependent on a concentration of the analyte in the detector chamber.

6. The sensor device of claim 1, wherein the receptor is an immobilized receptor.

7. The sensor device of claim 6, wherein the receptor is a receptor immobilized at the sensor electrode and/or at a surface of the detector chamber at the sensor electrode.

8. The sensor device of claim 1, wherein the electrical sensor further comprises at least one counterelectrode in addition to the sensor electrode, wherein the sensor device is configured to apply at least one electrical potential to the counterelectrode.

9. The sensor device of claim 1, wherein the sensor device further comprises at least one compensation sensor.

10. The sensor device of claim 1, wherein the electrical sensor comprises at least one field effect transistor, wherein the sensor electrode comprises at least one gate electrode of the field effect transistor.

11. The sensor device of claim 10, wherein the field effect transistor is an organic field effect transistor.

12. The sensor device of claim 1, wherein the sensor device further comprises at least one driving unit, wherein the driving unit is designed to detect the at least one electrical property of the electrical sensor.

13. The sensor device of claim 1, wherein the electrical sensor comprises at least one organic conductive or semiconducting material.

14. The sensor device of claim 13, wherein the sensor electrode comprises the at least one organic conductive or semiconducting material.

15. The sensor device of claim 13, wherein the organic conductive or semiconducting material is a conductive or semiconducting polymer.

16. A sensor system comprising the sensor device of claim 1, and at least one reader, wherein the sensor device and the reader are configured to communicate with one another.

17. The sensor system of claim 16, wherein the sensor device and the reader are configured to communicate wirelessly.

18. A method for detecting at least one analyte in a fluid, using the sensor device of claim 1, comprising:
connecting the detector chamber with the fluid in such a way that the analyte penetrates into the detector chamber; influencing at least one electrical property of the electrical sensor with the detector substance wherein the level of influence on the at least one electrical property is based upon a concentration of the analyte in the detector chamber; and
reversibly binding the analyte with the receptor.

19. A sensor device for detecting at least one analyte in a fluid, comprising at least one closed detector chamber and at least one electrical sensor comprising at least one sensor electrode, wherein the detector chamber can be connected to the fluid in such a way that the analyte can penetrate into the detector chamber, wherein the detector chamber comprises at least one detector substance, wherein the detector substance is configured to influence at least one electrical property of the electrical sensor, depending on a concentration of the analyte in the detector chamber, wherein the detector chamber accommodates at least one receptor, the receptor being formed by a substance distinct from the detector substance and wherein the receptor is configured to bind the analyte reversibly; and
wherein the detector substance comprises at least one detection reagent, wherein the detection reagent is configured to react with the analyte.

20. The sensor device of claim 19, wherein the detector substance comprises at least one enzyme.

21. A sensor device for detecting at least one analyte in a fluid, comprising at least one closed detector chamber and at least one electrical sensor comprising at least one sensor electrode, wherein the detector chamber can be connected to the fluid in such a way that the analyte can penetrate into the detector chamber, wherein the detector chamber comprises at least one detector substance, wherein the detector substance is configured to influence at least one electrical property of the electrical sensor, depending on a concentration of the analyte in the detector chamber, wherein the detector chamber accommodates at least one receptor, the receptor being formed by a substance distinct from the detector substance and wherein the receptor is configured to bind the analyte reversibly; and wherein the sensor device further comprises at least one compensation sensor and wherein the compensation sensor comprises at least one compensation sensor electrode, wherein the detector substance is connected to the sensor electrode, wherein the compensation sensor electrode is free of the detector substance.

22. A sensor device for detecting at least one analyte in a fluid, comprising at least one closed detector chamber and at least one electrical sensor comprising at least one sensor electrode, wherein the detector chamber can be connected to the fluid in such a way that the analyte can penetrate into the detector chamber, wherein the detector chamber comprises at least one detector substance, wherein the detector substance is configured to influence at least one electrical property of the electrical sensor, depending on a concentration of the analyte in the detector chamber, wherein the detector chamber accommodates at least one receptor, the receptor being formed by a substance distinct from the detector substance and wherein the receptor is configured to bind the analyte reversibly;

wherein the detector chamber comprises at least one membrane, wherein the membrane is configured to enable the analyte to penetrate into the detector chamber reversibly; and wherein the electrical sensor and a compensation sensor are linked into an electrical bridge circuit.

23. A sensor device for detecting at least one analyte in a fluid, comprising at least one closed detector chamber and at least one electrical sensor comprising at least one sensor electrode, wherein the detector chamber can be connected to the fluid in such a way that the analyte can penetrate into the detector chamber, wherein the detector chamber comprises at least one detector substance, wherein the detector substance is configured to influence at least one electrical property of the electrical sensor, depending on a concentration of the analyte in the detector chamber, wherein the detector chamber accommodates at least one receptor, the receptor being formed by a substance distinct from the detector substance and wherein the receptor is configured to bind the analyte reversibly; and wherein the detector chamber comprises at least one membrane, wherein the membrane is configured to enable the analyte to penetrate into the detector chamber reversibly and wherein the membrane is an analyte-specific membrane.

* * * * *